United States Patent
Fisher et al.

(12) 
(10) Patent No.: US 6,365,630 B1
(45) Date of Patent: Apr. 2, 2002

(54) COMPOSITIONS AND METHODS FOR INHIBITING PHOTOAGING OF SKIN

(75) Inventors: Gary J. Fisher; John J. Voorhees; Sewon Kang, all of Ann Arbor, MI (US)

(73) Assignee: Regents of the University of Michigan

(*) Notice: Subject to any disclaimer, the term of this patent is extended or adjusted under 35 U.S.C. 154(b) by 0 days.

(21) Appl. No.: 09/615,218

(22) Filed: Jul. 13, 2000

Related U.S. Application Data

(62) Division of application No. 09/089,914, filed on Jun. 3, 1998.
(60) Provisional application No. 60/057,976, filed on Sep. 5, 1997, and provisional application No. 60/048,520, filed on Jun. 4, 1997.

(51) Int. Cl.⁷ ............. A61K 31/20; A61K 7/42; A61K 31/035
(52) U.S. Cl. ............. 514/559; 424/59; 514/725
(58) Field of Search ................. 514/559, 725, 514/456, 629, 576; 424/59, 401

(56) References Cited

U.S. PATENT DOCUMENTS

| | | | |
|---|---|---|---|
| 4,455,368 A | | 6/1984 | Kojima et al. |
| 4,654,354 A | * | 3/1987 | Shroot et al. |
| 5,002,760 A | | 3/1991 | Katzev |
| 5,459,332 A | | 10/1995 | Carruthers |
| 5,609,854 A | | 3/1997 | Guerrero et al. |
| 5,614,178 A | * | 3/1997 | Bloom et al. |
| 5,618,522 A | * | 4/1997 | Kaleta et al. |
| 5,629,365 A | | 5/1997 | Razavi et al. |
| 5,710,177 A | | 1/1998 | Sauermann et al. |
| 5,780,042 A | * | 7/1998 | Gers-Barlag et al. |
| 5,824,702 A | | 10/1998 | Wei |
| 5,837,224 A | * | 11/1998 | Voorhees et al. |
| 5,916,910 A | | 6/1999 | Lai |
| 6,080,393 A | * | 6/2000 | Liu et al. |
| 6,153,176 A | * | 11/2000 | Kaleta et al. |

FOREIGN PATENT DOCUMENTS

| | | | |
|---|---|---|---|
| FR | 2528420 | * | 12/1983 |
| WO | WO93/10755 A1 | | 6/1993 |
| WO | WO96/23490 A1 | | 8/1996 |
| WO | WO96/41614 A1 | | 12/1996 |

OTHER PUBLICATIONS

Li et al., The Redox Active Components . . . , Experimental Eye Research, vol. 59/2, pp. 179–190. Aug. 1994.

Daphna–Iken et al., Interleukin–1. beta. induces . . . , American J. of Phy., vol. 269/6 38–6, pp. F831–F837, 1995.

Nikolowski et al., In vivo testing of antiinflammatory . . . , abstract, Dermatol. Monatsschr. 1982, vol. 168/3, pp. 173–181.*

Van Wauwe et al., Ketoconazole inhibits the in vitro and in vivo . . . , abstract, J. Pharmacol. exp. Ther., 1988, vol. 245/2, pp. 718–722.*

Braunhut et al., Retinoids modulate endothelial cell . . . , abstract, J/Biol. Chem., 1994, col. 269/18, pp. 13472–13479.*

* cited by examiner

*Primary Examiner*—William R. A. Jarvis
*Assistant Examiner*—Vickie Kim
(74) *Attorney, Agent, or Firm*—Bradley N. Ruben

(57) ABSTRACT

Compositions and methods are provided for ameliorating various effects of UVA and UVB radiation from the sun. The compositions including an ingredient that prevents photoaging from MED and subMED radiation, such as a retinoid, certain other compounds (such as N-acetylcysteine, 2-furildioxime, and vitamin C) and optionally other MMP inhibitors such as tetracyclines and/or compounds that inhibit the P-450-mediated metabolism of retinoids such as ketoconazole and other azole compounds. In the method, the composition is applied prior to exposure to the sun; depending upon the ingredients used in the composition, application should be from 7 to 48 hours prior to exposure. Compounds that prevent erythema (skin reddening, sunburn) do not necessarily protect against UV-mediated elevation of MMP levels and activity, and similarly compounds that prevent UV-mediated elevation of MMP levels and activity are not necessarily effective against UV-induced erythema.

11 Claims, 19 Drawing Sheets

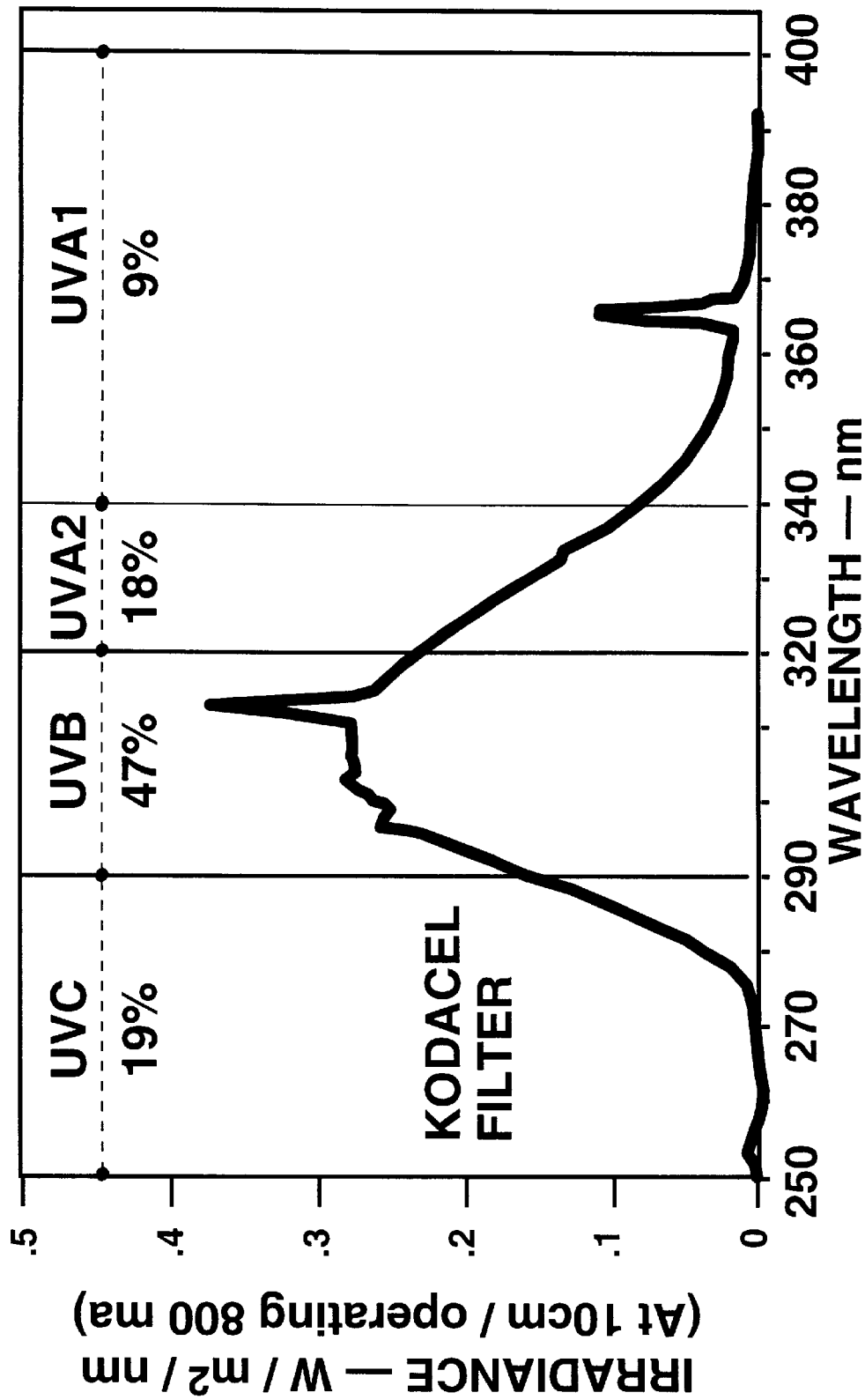

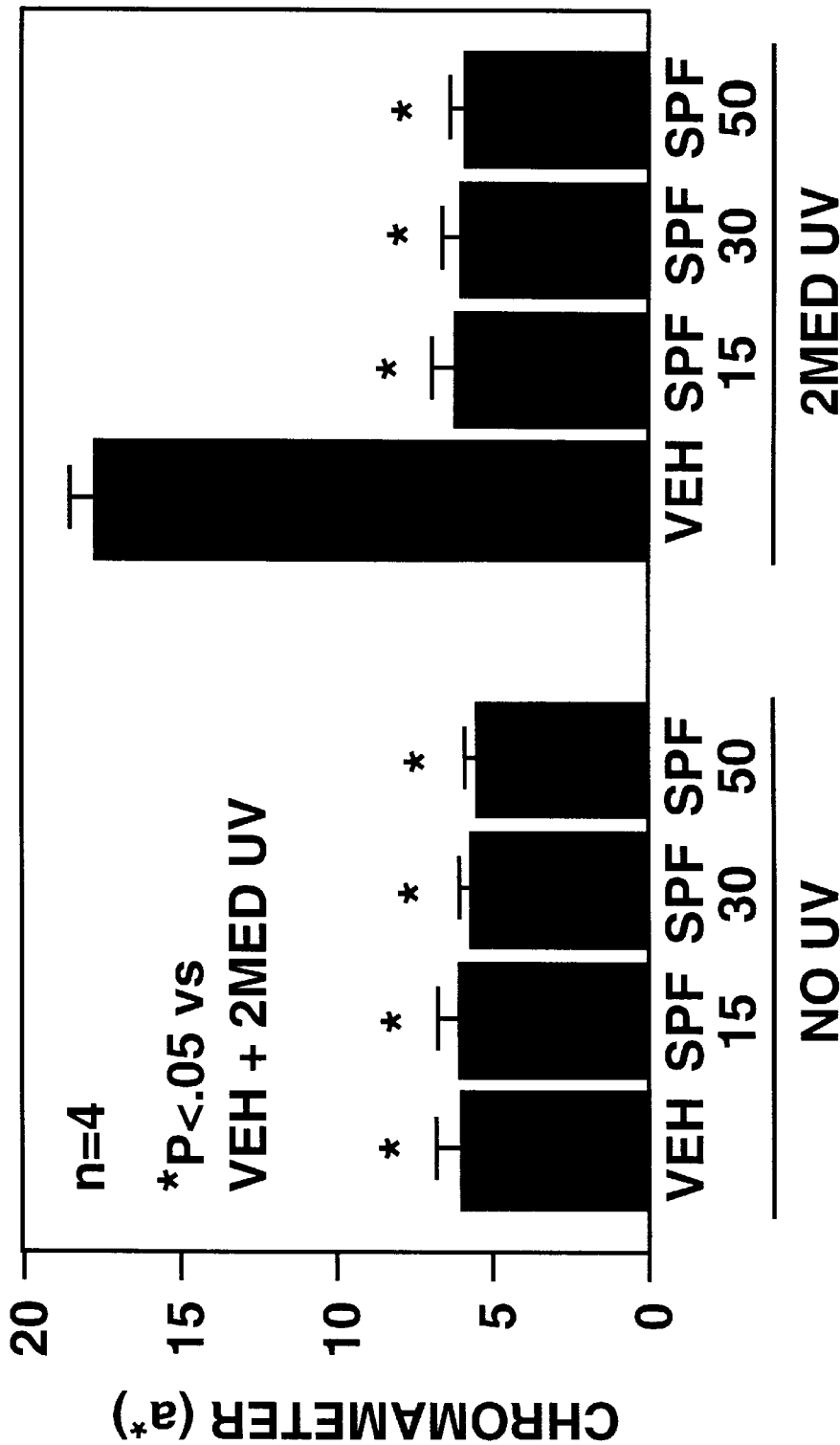

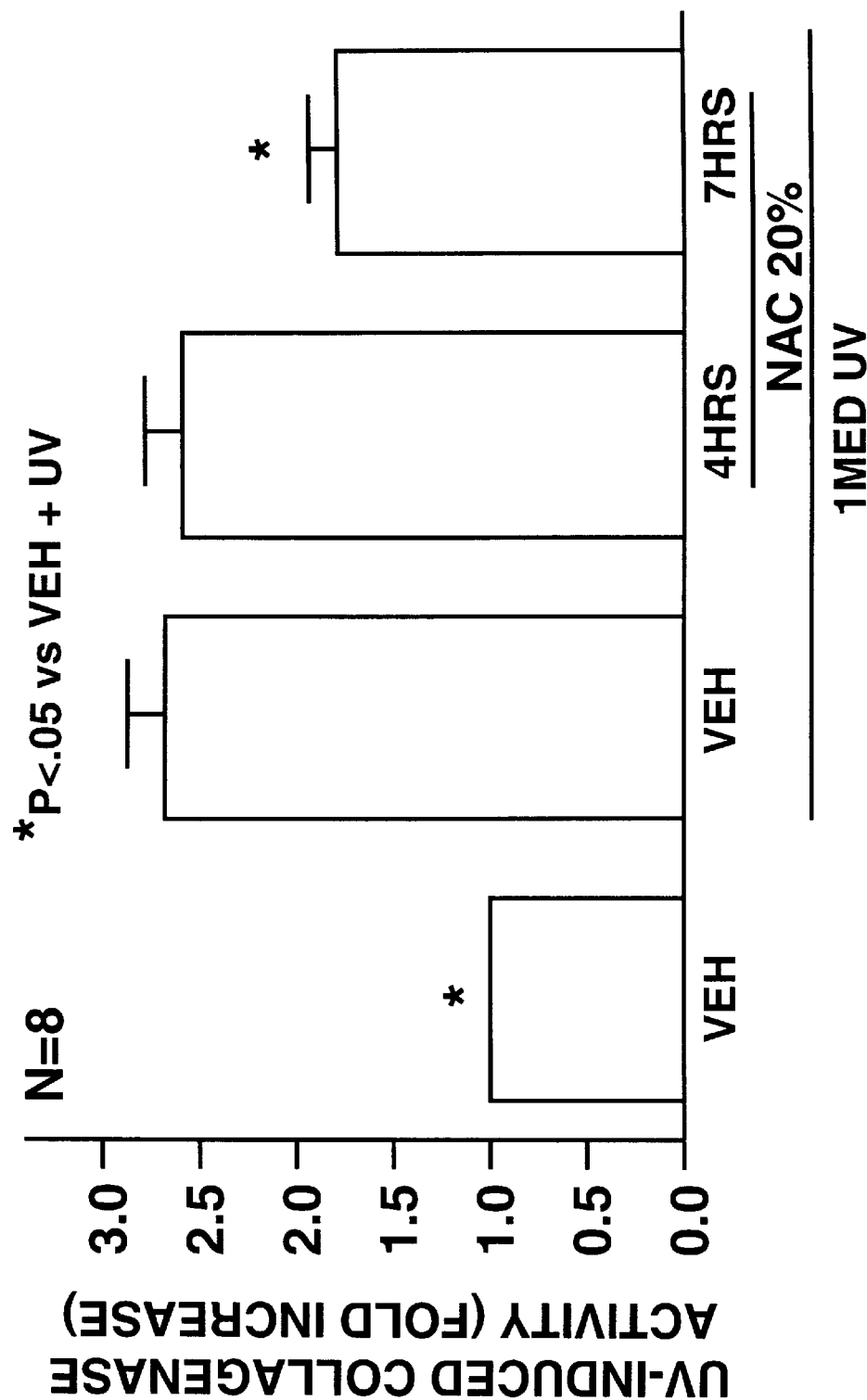

PARSOL® 1789 BLOCKS 2MED UV INDUCTION OF 92kDa GELATINASE ACTIVITY IN HUMAN SKIN *IN VIVO*

COMPOSITIONS AND METHODS FOR INHIBITING PHOTOAGING OF SKIN

This is a divisional application of Ser. No. 09/089,914 filed Jun. 3, 1998 which claims benefit of Ser. No. 60/048,520 filed Jun. 4, 1997 and claims benefit of Ser. No. 60/057,976 filed Sep. 5, 1997.

TECHNICAL FIELD

This invention involves photoprotection of human skin. More particularly, the invention relates to compositions for topical application and to methods for using the same to inhibit photoaging of skin, especially as induced by exposure to incidential and/or direct radiation as would occur daily. Separately, this invention provides novel methods and compositions for reducing UV-induced erythema (skin reddening).

BACKGROUND

Photoaging is a term presently used to describe the changes in appearance and/or function of human skin as a result of repeated exposure to sunlight, and especially regarding wrinkles and other changes in the appearance of the skin.

Solar radiation reaching the earth's surface that effects and enables various animals, including humans, comprises ultraviolet (UV) ($\lambda$<400 nm), visible (400 nm<$\lambda$<700 nm), and infrared (IR) ($\lambda$>700 nm). UV radiation is generally divided into UVA (320–400 nm), UVB (290–320 nm), and UVC (<290 nm); UVC radiation is blocked from reaching the earth's surface by stratospheric ozone. The ultraviolet (UV) component of sunlight, particularly UVB, is generally believed to be the principal causative agent in photoaging.

The extent of UV exposure required to cause photoaging is not currently known, although the amount required to cause erythema (reddening, commonly seen as sunburn) in human skin is known and quantified empirically as the "minimal erythemal dose" ("MED") from a given UV source. UVB wavelengths of 290–300 nm are the most erythmogenic. The effectiveness of UV radiation in causing erythema decreases rapidly as the UV wavelength is increased beyond about 300 nm; wavelengths of 320 nm and 340 nm are, respectively, one hundred and one thousand times less potent at causing skin reddening than wavelengths of about 298 nm. Repeated exposure to sunlight at levels that cause erythema and tanning are, nevertheless, commonly associated with photoaging. Erythema from UVB is suggested to be a function of the total radiation exposure, not the intensity of the radiation exposure. According to *Physiology, Biochemistry, and Molecular Biology of the Skin*, 2nd Ed., ed. by L. A. Goldsmith (New York: Oxford Univ. Press, 1991), UVA is considered both melanogenic and erythemogenic and UVA exposure induces synthesis of a 32 kDa stress protein in human skin, as well as immediate erythema not apparent after UVB exposure.

Photoaging in human skin is characterized clinically by coarseness, wrinkles, mottled pigmentation, sallowness, laxity, eventually premalignant, and ultimately malignant neoplasms. Photoaging commonly occurs in skin that is habitually exposed to sunlight, such as the face, ears, bald areas of the scalp, neck, forearms, and hands.

Sunscreens are commonly used to prevent photoaging of skin areas that are exposed to sunlight. Sunscreens are topical preparations that contain ingredients that absorb, reflect, and/or scatter UV light. Some sunscreens are based on opaque particulate materials, among them zinc oxide, titanium oxide, clays, and ferric chloride. Because such preparations are visible and occlusive, many people consider these opaque formulations cosmetically unacceptable. Other sunscreens contain chemicals such a p-aminobenzoic acid (PABA), oxybenzone, dioxybenzone, ethylhexyl-methoxy cinnamate, octocrylene, octyl methoxycinnamate, and butyl-methoxydibenzoylmethane that are transparent or translucent on the skin. While these types sunscreens may be more acceptable cosmetically, they are still relatively short-lived and susceptible to being removed by washing or perspiration.

As noted above, the generally accepted etiology of photodamage to skin involves an exposure to sunlight sufficient to cause erythema (sunburn or reddening; literally a flush upon the skin), and it is now known that sufficient UVB radiation does cause erythema. This philosophy dictates that present compositions and methods for inhibiting photoaging include the use compounds that block or absorb UVB, and that such compositions need be used only when there is sufficient likelihood that exposure to sunlight will result in erythema. More recent sunscreen compositions include combinations of compounds that block both UVA and UVB radiation.

It has been suggested that UV solar radiation induces reactive oxygen species (ROS) in the skin. Rieger, M. M. *Cosmetics and Toiletries* (1993) 108:43–56 reviews the topical application of known antioxidants to the skin for reducing the presence of ROS.

Retinoids have been used as therapy to improve the appearance of sun-damaged skin. U.S. Pat. No. 4,877,805 describes the treatment of photoaged skin. The patent indicates that there is little point in beginning the application of a retinoid to treat photodamage until the effects of aging begin to appear. Several studies have investigated improving the appearance of existing photodamaged skin with the use of all-trans retinoic acid. G. D. Weinstein et al., "Topical Trentinoin for Treatment of Photodamaged Skin," *Arch. Dermatol.*, 127:659–665 (May 1991); J. S. Weiss et al., "Topical Tretinoin Improves Photoaged Skin," *J. Amer. Med. Assn.*, 259(4):527–532 (Jan 22/29, 1988).

Matrix metalloproteinases (MMPs) are a family of enzymes that play a major role in physiological and pathological destruction of connective tissue, especially collagen. Various types of collagen and collagenases (types of MMPs) are known in this field, and a further description can be found in our copending U.S. patent application. Ser. No. 08/588,771, filed Jan. 19, 1996, the disclosure of which is incorporated herein by reference in its entirety and for all purposes. Inhibitors of MMPs (i.e., direct inhibitors of the proteinase) and of molecular pathways (i.e., inhibitors of AP-1) that affect MMP expression are known in other fields and likewise are described in the aforementioned application No. 588,771.

In summary, the state of the art considers that photodamage is caused primarily by UVB radiation, and that presently available sunscreens are sufficient to prevent photodamage. "Dr. Ceilley [current President fo the American Academy of Dermatology] believes that staying out of the sun and using sunscreen could have prevented many of the skin cancers that he treats in his practice, as well as the premature wrinkles that his patients are concerned about." Skin SAVVY, Amer. Acad. Dermat. supp. to *USA Today*, May 1997.

SUMMARY OF THE INVENTION

The present invention is based, in one preferred embodiment, on our discovery that suberythemal doses of UV radiation induce MMPs that degrade skin connective tissue and thus are likely responsible for photoaging. That is, we have discovered that UV radiation exposures insufficient to cause erythema nevertheless induce MMPs which degrade dermal connective tissues, such as collagen and elastin, presumed to cause photodamage. That is, a UV exposure (with UVA and/or UVB) insufficient to cause erythema nevertheless is sufficient to cause photodamage via MMP induction. As such, the term "photodamage" should be redefined in the art so as not to require erythema. Thus, a combination of UVA and/or UVB radiation can significantly damage the skin. Our invention broadly includes preventing photodamage from UVA and/or UVB radiation, especially before clinical signs of photodamage are presented.

In our preferred embodiments, retinoids are used to prevent photodamage. In another embodiment of this invention, we have found that various other compounds are useful in preventing photodamage by inhibiting the production and/or activity of MMPs. Though some of these compounds are termed "antioxidants" and may prevent erythema, they also may reduce the concentration of MMPs in UV-exposed human skin. Separately, our results testing such compounds show that prevention of erythema does not correlate with inhibiting UV-mediated increases in MMPs.

In yet another embodiment of this invention, we have found that retinoids can inhibit the elevated MMP levels due to UV-exposure on human skin. While the prior art teaches that retinoids are useful for the treatment and repair of photodamaged skin, we have discovered that retinoids can interfere with the UV-induced elevation of MMP levels, and so retinoids can be used prophylatically to prevent photodamage from occuring.

In summary, then, one embodiment of our invention comprises a composition, especially for daily use, comprising a UVA blocker, a UVB blocker, and an MMP inhibitor in a topically acceptable carrier.

Also included is a method for preventing incidental photodamage, a prophylactic against photodamage where incidental UV exposure does not produce erythema, by the topical application of a composition comprising a UVA blocker, a UVB blocker, and an MMP inhibitor, to normally exposed skin (such as the face, head, hands, and forearms).

Yet another embodiment of our invention is a composition, especially for prophylactic use against photodamage, comprising an erythema inhibitor and an MMP inhibitor.

In another embodiment our invention is directed to window structures having a coating thereon or admixed therewith a UVA blocker and a UVB blocker. As used herein, a blocker is broadly a compound that blocks the direct effects of radiation on the skin by absorbing, reflecting, or modulating to a non-harmful wavelength the particular light.

In still another embodiment of this invention, in those compositions in which a retinoid is present, the composition preferably further comprises a compound that inhibits the breakdown of the retinoid in the skin. Such compounds are those that inhibit the cytochrome P-450-mediated breakdown of retinoids.

BRIEF DESCRIPTION OF THE DRAWINGS

FIG. 6 depicts the spectrum emitted by the illumination apparatus used for the experiments herein (except that having results shown in FIG. 5).

FIG. 7 depicts the results topically applied commercial sunscreens had on erythema induction after 2 MED UVB/UVA exposure of human skin.

FIGS. 11A–11B depict the effect of the time of pretreatment of skin with NAC on the efficacy of NAC to inhibit UV-induced collagenase and gelatinase.

DETAILED DESCRIPTION OF PREFERRED EMBODIMENTS

The present invention is directed to inhibiting (i.e., reducing or preventing) photoaging of skin, especially human skin. Treatment according to this invention is preferably practiced on skin such as that of the head, neck, hands, and arms that in typical, everyday living are habitually exposed to sunlight. Because repeated exposure to doses of UV below those that cause erythema can lead to photoaging, the invention should be practiced on skin subject to such low dose exposure.

UVB doses in the range of 30–50 mJ/cm$^2$ skin cause erythema in most fair-skinned people. Accordingly, the invention will prevent photoaging of skin subjected to doses below this range (typically above about 5 mJ/cm$^2$ which is equivalent to a few minutes of sunlight exposure). Sunlight reaching the surface of the earth when the sun is essentially overhead provides the following amounts of radiation: 0.5% UVB; 6.5% UVA; 38.9% visible light; and 54.0% IR. These radiation types provide the following energy fluxes: 2.11 mJ/cm$^2$·s (21.1 W/m$^2$) for UVB; 8.57 mJ/cm$^2$·s (85.7 W/m$^2$) for UVA; 53.2 mJ/cm$^2$·s (532 W/m$^2$) for visible light; and 72.2 mJ/cm$^2$·s (722 W/m$^2$) for IR.

Figure 1:
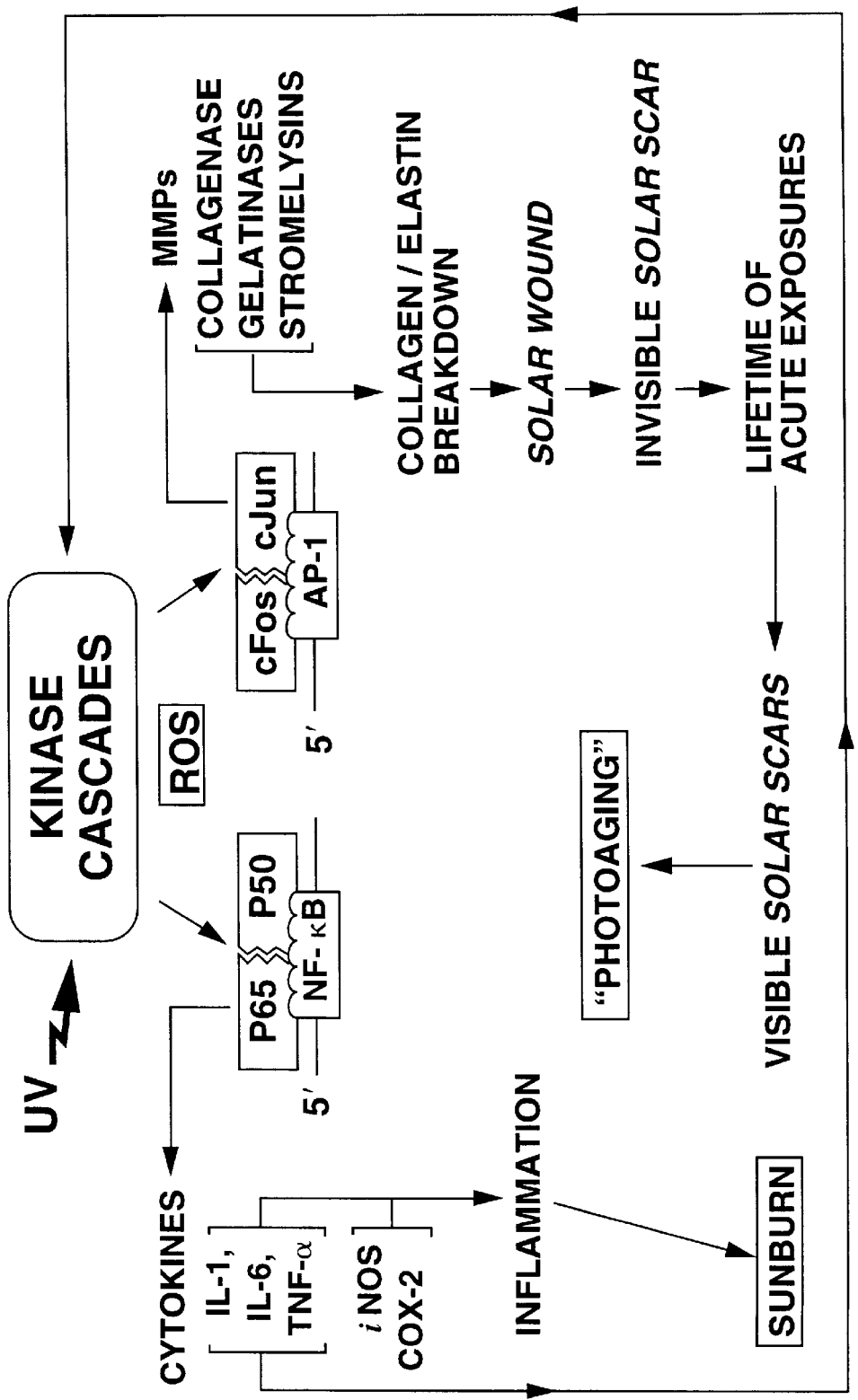
FIG. 1 is depicts what is believed to be the general pathways for skin damage due to UV exposure based on our discoveries.

While not desirous of being constrained to a particular theory, the following examples may be better appreciated with reference to FIG. 1, which depicts an overview of some of the UV-induced biochemical pathways leading to changes in the skin. As shown, UV radiation induces a MAP kinase cascade from which two resulting pathways are shown: one results in induction of interlukins, which lead to erythema; the other results in induction of MMPs, which lead to connective tissue degradation. While the art has considered these results as due to UVB radiation, we have now shown in a series of experiments that UVA is a definitive culprit in photodamage even when UV-exposed skin provides no visual clues of photodamage. It should be understood in connection with this application, however, that both UVA and UVB are responsible, possibly even independently, for UV-mediated induction of MMPs in human skin after exposure to solar radiation.

Exposure to UV radiation is typically measured in these arts by reference to the minimal erythemal dose, MED, which is defined as an exposure to UV radiation sufficient to cause reddening of the skin. One (1) MED is equivalent generally to about 30 mJ/cm$^2$·s of solar radiation. The philosophy of the prior art is that exposure to natural sunlight sufficient to cause redness (sunburn, erythema) initiates photoaging. Using the UV source described below, which emits both UVA and UVB radiation (with a lower ratio of UVA/UVB than found in natural sunlight), we have confirmed that if skin redness is induced then MMPs are also induced. Thus, the present philosophy of the art is that sunscreens should be used because they prevent redness and so prevent photoaging.

We believe we have contradicted some of the present philosophy and have also found unexpectedly the effect on human skin of various UV exposures and the use of various compounds applied prior to exposure. One of our unexpected results is that UV exposure insufficient to cause skin redness nevertheless induces increased MMP activity (and so photoaging) in human skin. Thus, conventional sunscreens may prevent redness but may not prevent photoaging from the increase in MMP activity after UV exposure. We have also identified compounds that prevent redness, which is important not only to prevent the pain and discomfort caused by erythema, but also possibly for compliance by including an erythema inhibitor in a composition that inhibits photoaging (because a patient may tend to believe the antiphotoaging component of the composition is not effective if erythema results after use of a composition touted as preventing photodamage).

Another unexpected finding is that blocking UVA radiation prophylactically inhibits both increased MMP activity and increased cJUN protein concentration in UV-exposed human skin, and so is a prophylactic against photoaging. Combined with our finding that suberythemal UV exposure causes photoaging, one aspect of our invention contemplates the daily use of a UVA blocker as a prophylactic against photoaging. Because UVB also induces MMPs, a more preferred composition would include both a UVA and a UVB blocker.

Still another unexpected finding is that pretreatment of skin with a retinoid mitigates the increased MMP activity typically occurring after UV exposure. Accordingly, our invention contemplates a composition for topical application prior to UV exposure that contains a retinoid as a prophylatic against photoaging.

Yet another unexpected finding of our investigations is that certain compounds (some having been reported to have antioxidant properties) provide a good anti-erythemal sunscreen effect, although they do not appear to inhibit increased MMP activity subsequent to UV exposure.

The invention is now described with reference to the figures. The details of the experiments from which the results shown in the figures were obtained, as well as the apparatus used to irradiate our human volunteers, and the immunohistological methods are described below. The area of the volunteers' skin tested is typically hidden or physically protected from the sun exposure during most of one's life (e.g., skin from the hips and buttocks). As noted from the results of our investigation, one cannot rely solely on in vitro experimentation to determine whether a compound is an MMP inhibitor and is also suitable for use as an inhibitor in vivo. Accordingly, one must test such compounds by methods as described herein to determine whether such compounds provide the desired therapeutic effect.

Figure 2:
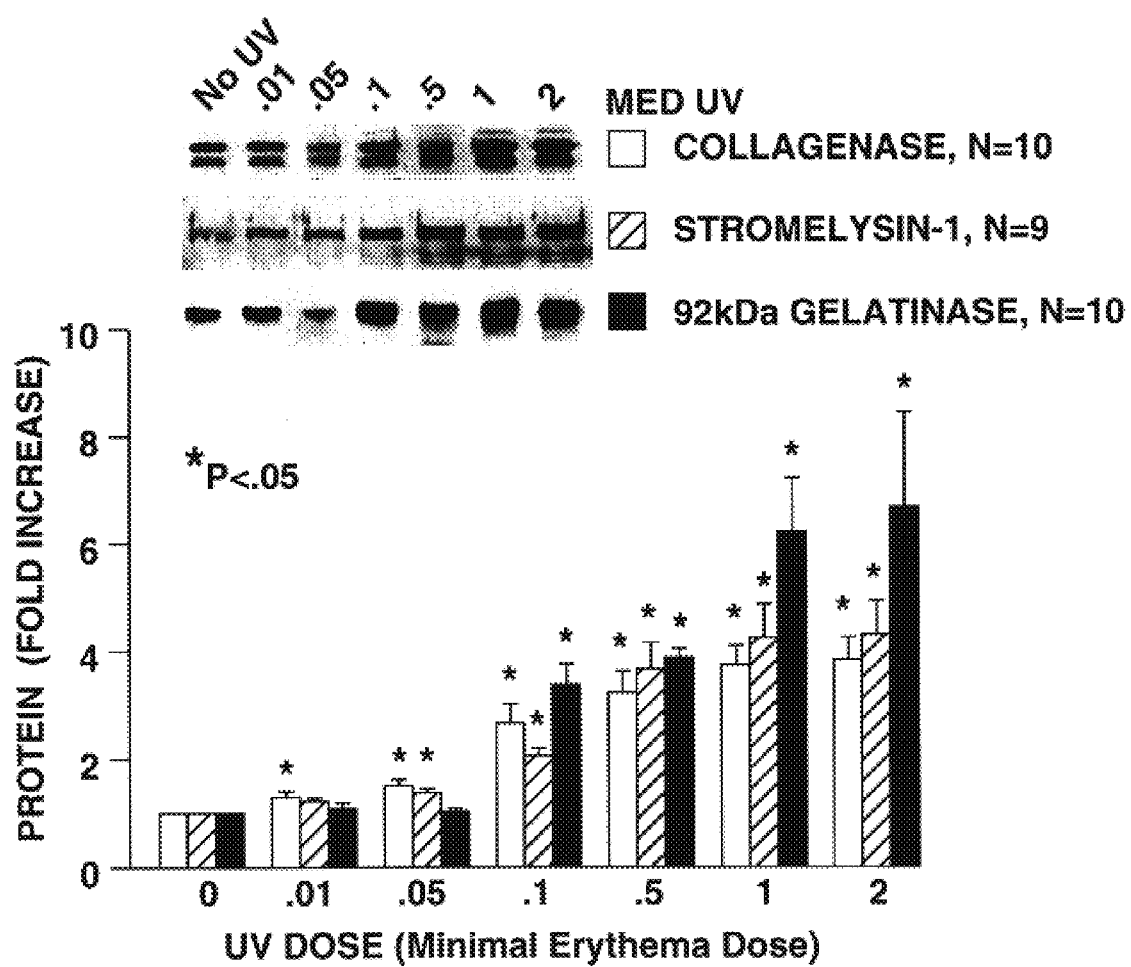
FIG. 2 depicts evidence that suberythemal UVB/UVA radiation induces collagenase, stromelysin-1, and the 92 kDa gelatinase, all MMPs; the histogram is a quantitive representation of the radioblot test for each of these proteins.

FIG. 2 depicts evidence that suberythemal UV exposure induces the collagenase, stromelysin-1, and the 9 skDa gelatinase MMPs. Portions of volunteers' skin was exposed to the following amounts of UV radiation expressed as a fraction of one (1) MED: 0.01, 0.05, 0.1, 0.5, 1, and 2. Biopsies and subsequent radioassays reveal (as shown in the radioblot in the figure, which is represented quantitatively by the histogram) that one-half of an MED is sufficient to induce MMPs; even 0.1 MED is sufficient to elevate the production of MMPs significantly above baseline levels; and 0.01 MED is sufficient to elevate collagenase above the baseline level. Thus, FIG. 2 shows that suberythemal UV radiation causes the production of MMPs. Nevertheless, it might be assumed that human skin returns to a baseline state where the levels of MMPs are not elevated, especially after exposure to low doses of UV radiation.

Figure 3:
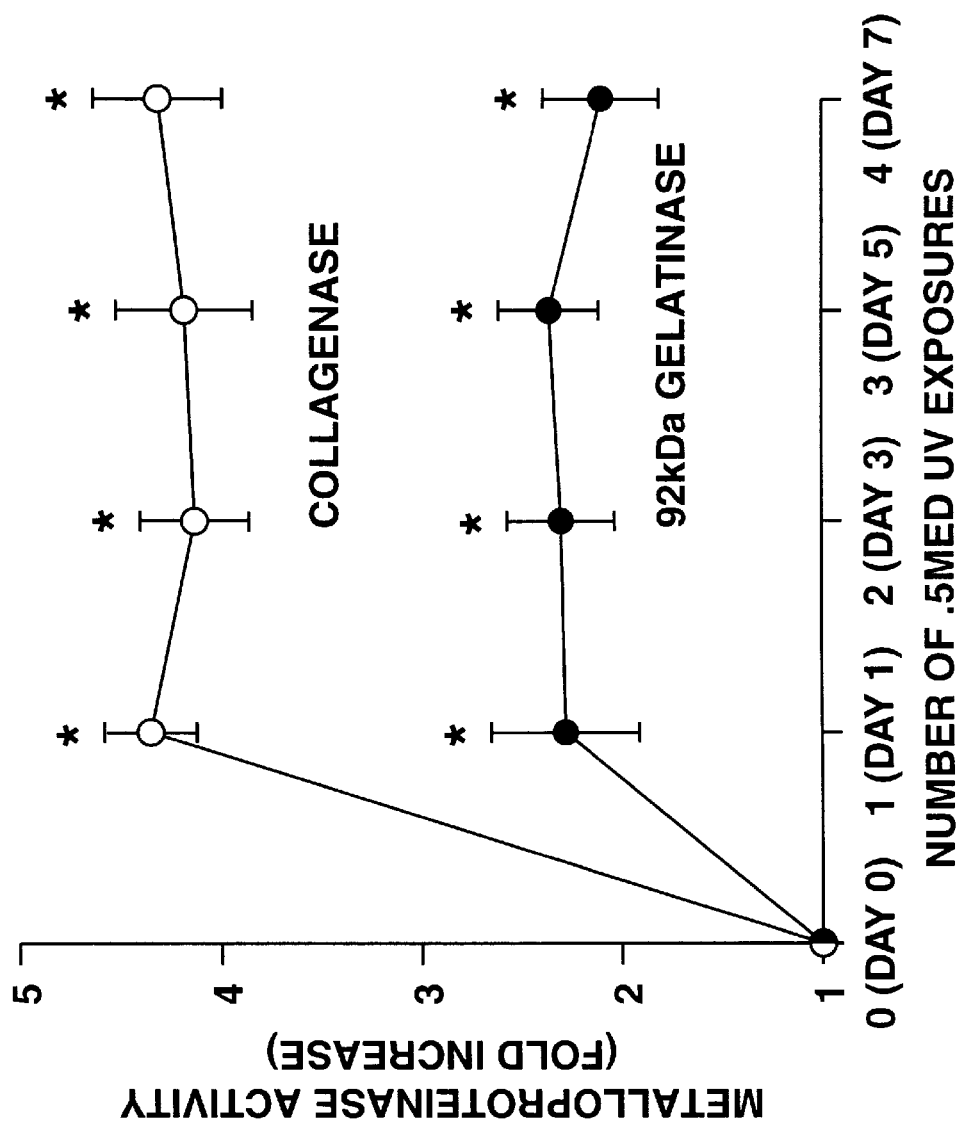
FIG. 3 depicts evidence that regularly repeated suberythemal UVB/UVA exposure of human skin induces consistently elevated levels of the 92 kDa gelatinase and collagenase MMPs.

FIG. 3 presents further evidence that repeated exposure to suberythemal UV radiation generates MMPs and that these levels remain elevated over time. When people were irradiated with one-half MED every two days, the level of MMPs remained elevated, and so collagen is continuously broken down by repeated, subMED exposure to UV radiation. FIG. 3, combined with the knowledge that very small UV doses induce MMPs as shown in FIG. 2, implies that daily, subMED, yet chronic exposure to UV radiation causes elevated MMP levels in human skin, and thus one's skin may never fully recouperate from chronic subMED UV exposure.

Figure 4:
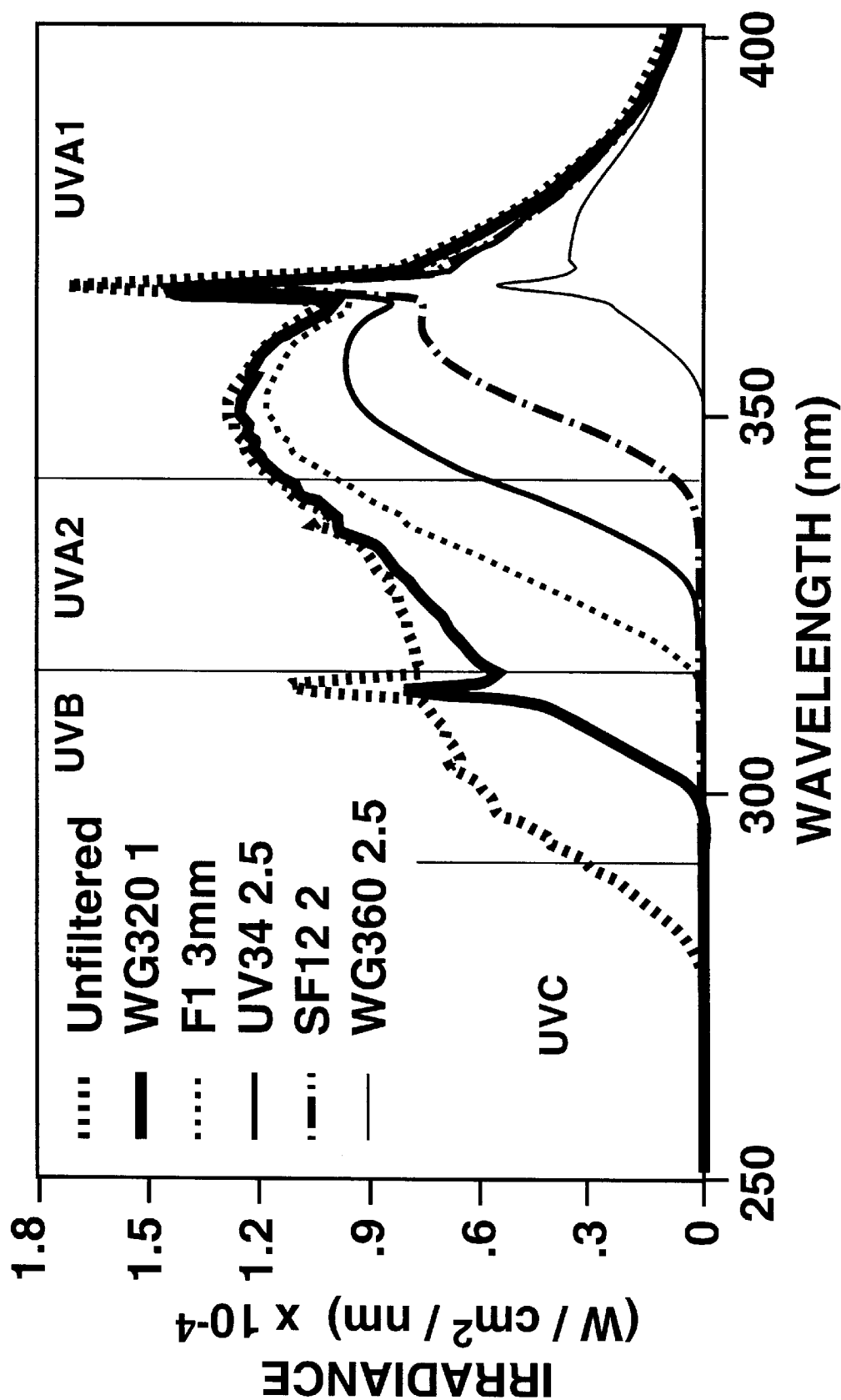
FIG. 4 depicts the spectrum emitted by an illumination apparatus, both unfiltered and through five different filters, used for the results depicted in FIG. 5.

FIG. 4 depicts the spectrum emitted from the illumination apparatus unfiltered and with various conventional filters (WG320 1; F1 3 mm; UV34 2.5; SF12 2; and WG360 2.5). The spectrum emitted from the apparatus through the various filters is shown by the different types of lines. The WG320 1 filter can be considered to approximate the sun with both UVB, UVA2, and UVA1 radiation, whereas the WG360 2.5 filter allows only UVA1 radiation to pass through. This apparatus includes both UVB lamps (Philips model TL40W/12/RS, available from Ultraviolet Resources Inc., Lakewood, Ohio) and UVA lamps (Q-Panel UVA-351, available from Q-Panel Lab Products, Cleveland, Ohio).

Figure 5:
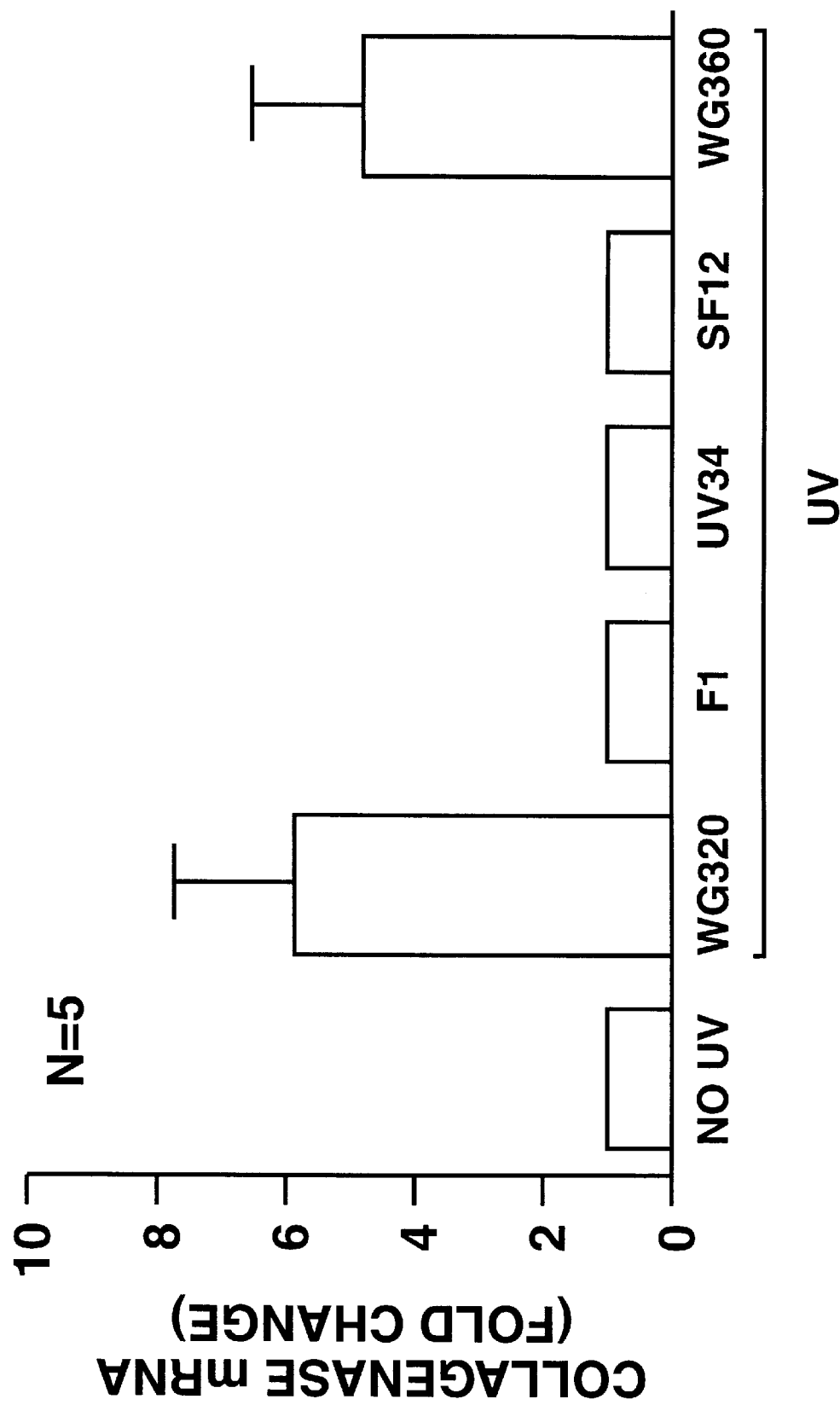
FIG. 5 depicts the induction of collagenase in human skin as a function of UV wavelength (through the various filters shown in FIG. 4) wherein a constant amount of energy was delivered.

We tested for the induction of collagenase as a function of wavelength when the person was irradiated with a constant amount of energy. Given the curves shown in FIG. 4, the relative durations during which a volunteer was exposed under a given filter can be determined by the ratio of an integration of the areas under each of the curves as a function of the wavelengths emitted; thus, even though the same amount of energy was delivered to the subject, the duration of the exposure under the WG360 2.5 filter was longer than under the WG320 1 filter. The results shown in FIG. 5 imply that a combination of UVB and UVA induces collagenase (filter WG320 1), and that UVA1 alone (filter WG360 2.5) is also sufficient to induce collagenase. At early and late times of day when the sun is low on the horizon, the proportion of UVA to UVB is actually increased, and so skin is exposed to more UVA radiation than it would be at noon time. Thus, the results shown in FIG. 5 that UVA1 is sufficient to cause elevated MMPs, which occurs at early and late times of day when sun exposure does not cause erythema, indicates that photodamage still occurs at those times of day, even in the absence of erythema. Also, contrary to what the average person would consider to be a "safe" time of day to be out in the sun because sunburn is unlikely to occur, nonetheless is not safe because MMPs still can be induced by the sun's UV radiation.

Figure 8A:
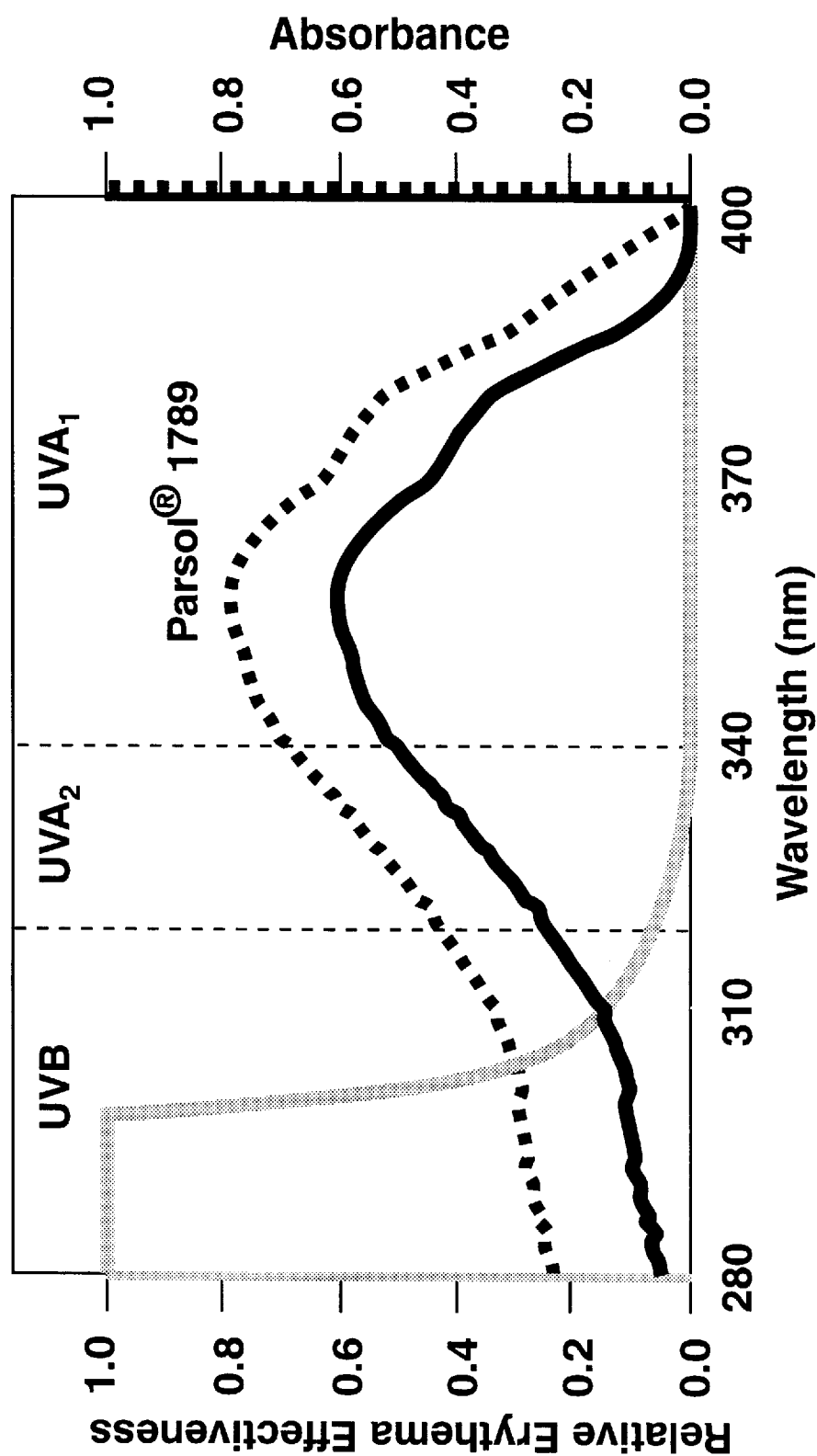
FIGS. 8A and 8B depict the UV absorbance of a UVA blocker and the effect of pretreatment with such blocker on erythema in UV-exposed human skin.
Figure 8B:
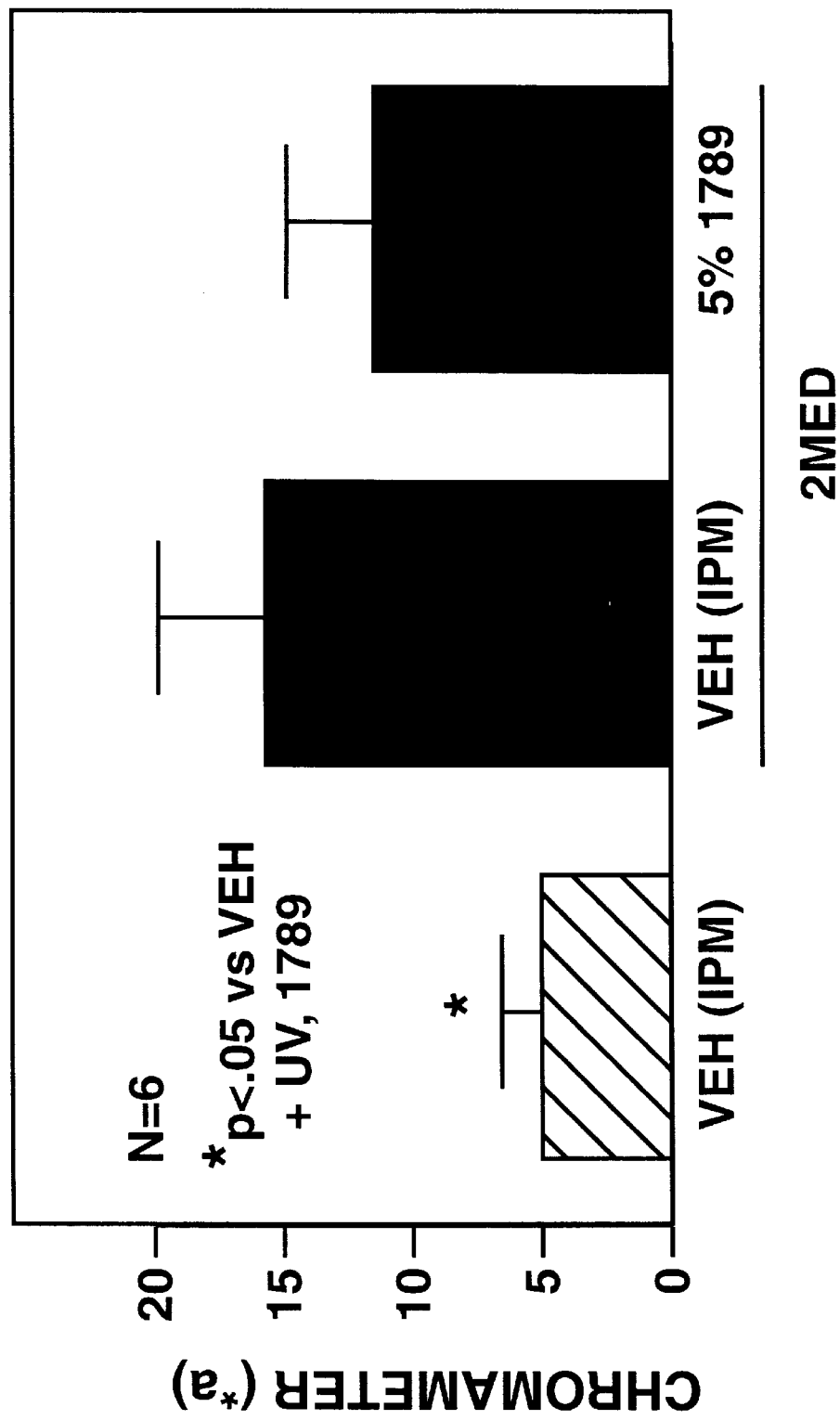

The erythema response is of clinical importance because, at the very least, significant pain and discomfort occurs. Various over-the-counter sunscreens do provide protection against erythema, as shown in FIG. 7. Typically these sunscreen contained only a UVB blocker, although many are now marketed with a "UVA" blocker. The blocking spectrum of a commercially available UVA blocker, PARSOL 1789, is shown in FIG. 8A; the right hand vertical scale correlates with the absorbance characteristics of the blocker, and left vertical scale correlates with the relative effectiveness of the blocker in preventing erythema at wavelengths generally greater than about 300 nm. This UVA blocker does provide some protection against 2 MED from our standard source (FIG. 8B).

Various other compounds have been used to prevent erythema. We tested a number of different compounds, which were applied to skin about seven hours prior to UV exposure and subsequent biopsy, for the effectiveness in preventing UV-induced skin redness. Melatonin does appear to prevent erythema at irradiation doses of above about 2 MED. Vitamin E was slightly worse but still very effective at preventing erythema. Acetylsalicylic acid (ASA) and vitamin C also provided protection against erythema induced from one MED when applied 16 hours prior to exposure. FDO is also effective at preventing erythema. NAC apparently had no effect against erythema.

Figure 9:
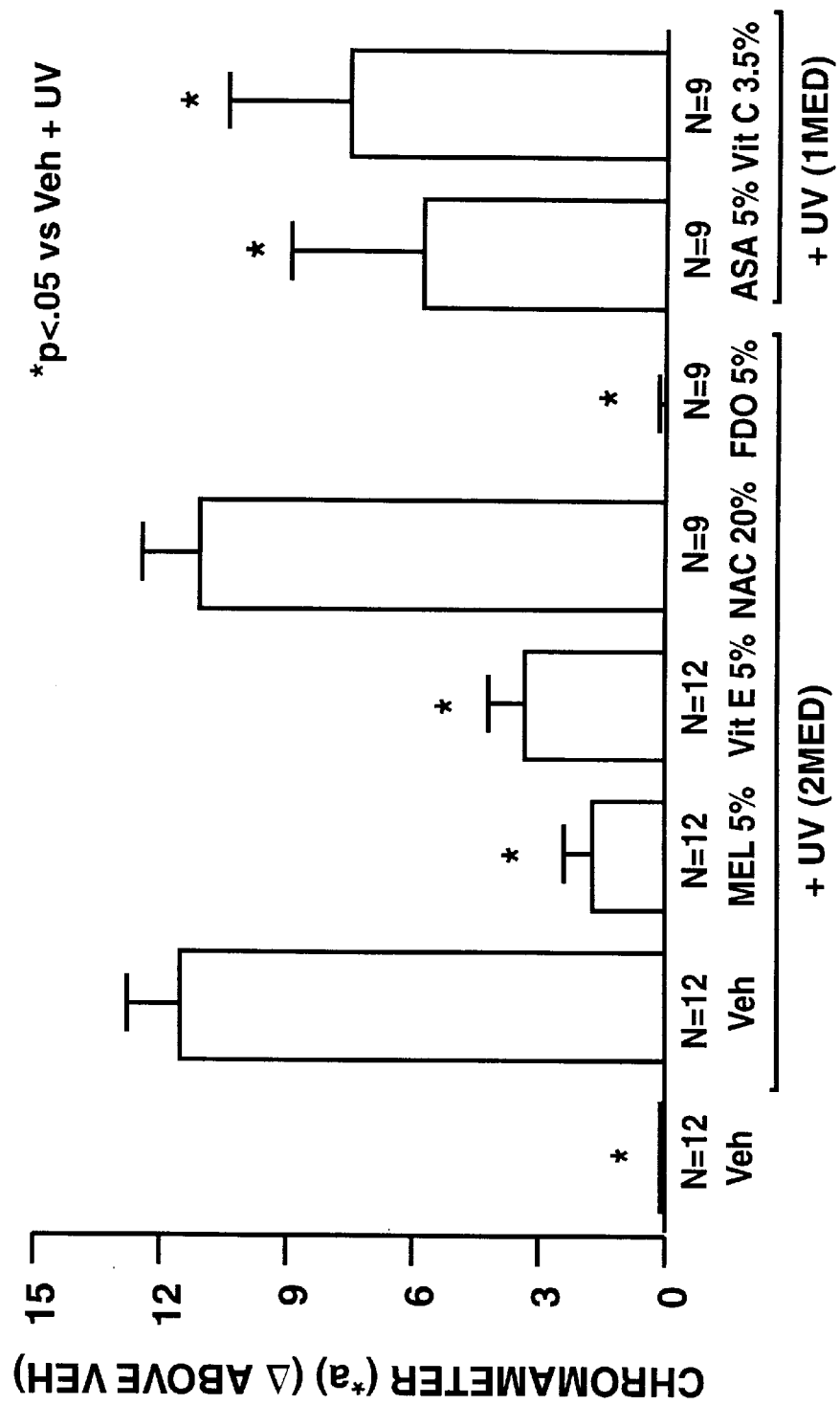
FIG. 9 depicts the effects of melatonin, vitamin E, N-acetyl cysteine (NAC), and 2-furildioxime (FDO) on preventing erythema from exposure to two MEDs of radiation, and of acetylsalicylic acid (ASA) and vitamin C on preventing erythema from exposure to one MED of radiation in human skin.

Based on the results shown in FIG. 9, one of our inventions is a method for preventing erythema by applying to skin that will be exposed to UV radiation (i) melatonin and/or vitamin E (or a derivative of either) at least about 7 hours prior to exposure, and/or (ii) acetylsalicylic acid, vitamin C, and/or FDO (or a derivative of any thereof) at least 16 hours prior to exposure.

Figure 10:
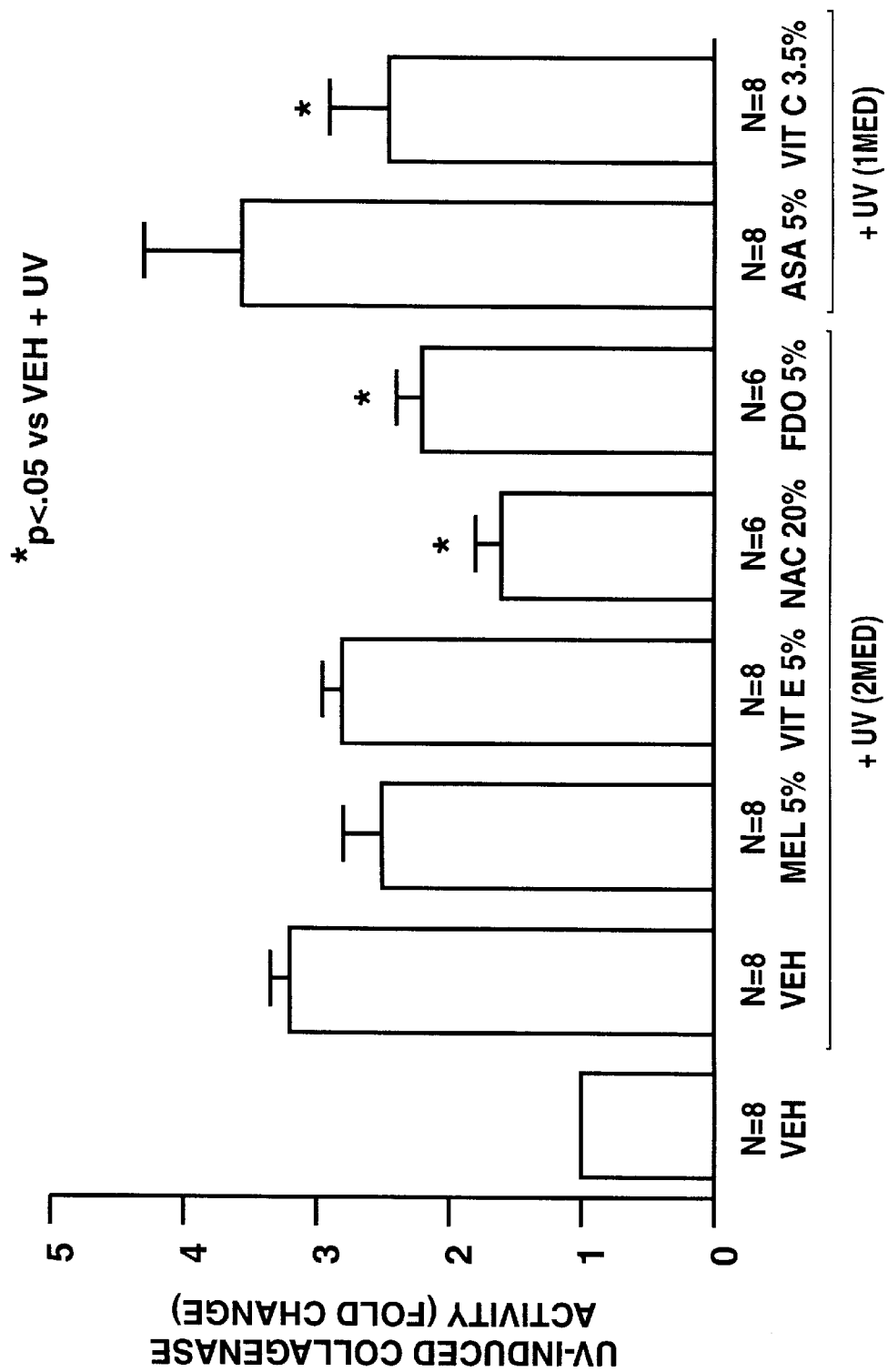
FIG. 10 depicts the effects of melatonin, vitamin E, N-acetyl cysteine (NAC), and 2-furildioxime (FDO) on preventing elevated collagenase activity from exposure to two MEDs of radiation, and of acetylsalicylic acid (ASA) and vitamin C on preventing elevated collagenase activity from exposure to one MED of radiation in human skin.
Figure 11A:
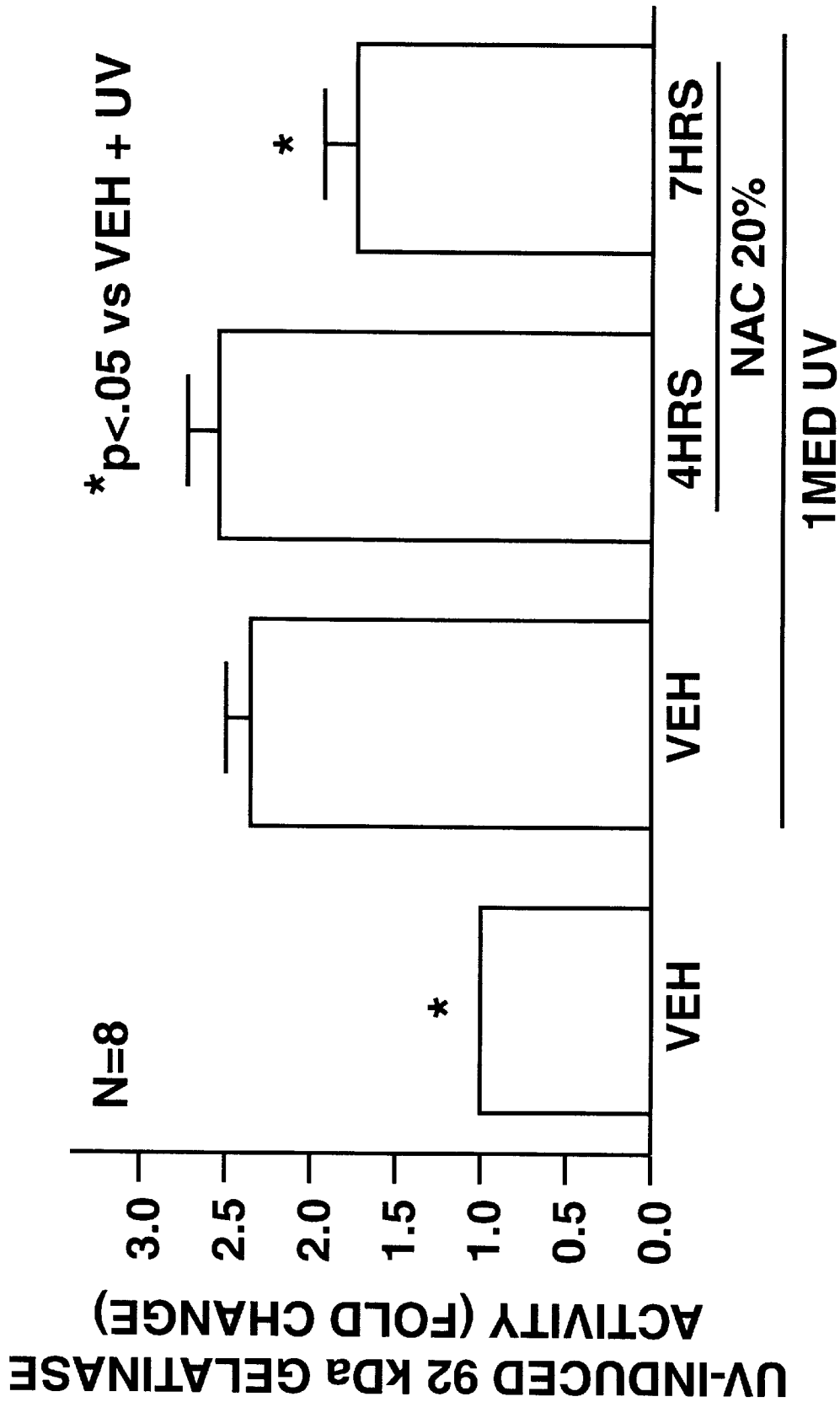

Having investigated and described various anti-erythematic compounds (FIG. 9), these compounds were tested to determine if prevention of erythema was indicative of prevention against elevated levels of MMPs, the results of which are shown in FIG. 10. Although good at preventing sunburn, neither melatonin nor vitamin E (both with pretreatment) prevented induction of MMPs such as the 92 kDa gelatinase and collagenase after exposure to 2 MEDs. Likewise, although useful at preventing sunburn, ASA was not effective at preventing elevated collagenase activity. Unexpectedly, NAC, which was not effective at preventing erythema, was effective at preventing increased MMP activity after exposure to two MED. We also discovered that the use of NAC to prevent increased MMP levels (such as the 92 kDa gelatinase and collagenase) requires pretreatment for more than four hours, and preferably at least about seven hours prior to exposure (one MED; FIGS. 11A and 11B).

In retrospect, compounds that prevented an erythemogenic response (melatonin, vitamins C and E, FDO, and ASA) were not necessarily also effective at preventing a UV-induced increase in collagenase activity (comparing FIGS. 9 and 10). On the other hand, compounds apparently not effective for preventing erythema (e.g., NAC) can be useful for preventing the UV-mediated increase in MMPs. Thus, another invention is the use of NAC, FDO, or vitamin C (or a derivative of any) to prevent UV-induced elevation of MMPs such as the 92 kDa gelatinase and collaganese, applied at least about seven hours prior to exposure.

Figure 12:
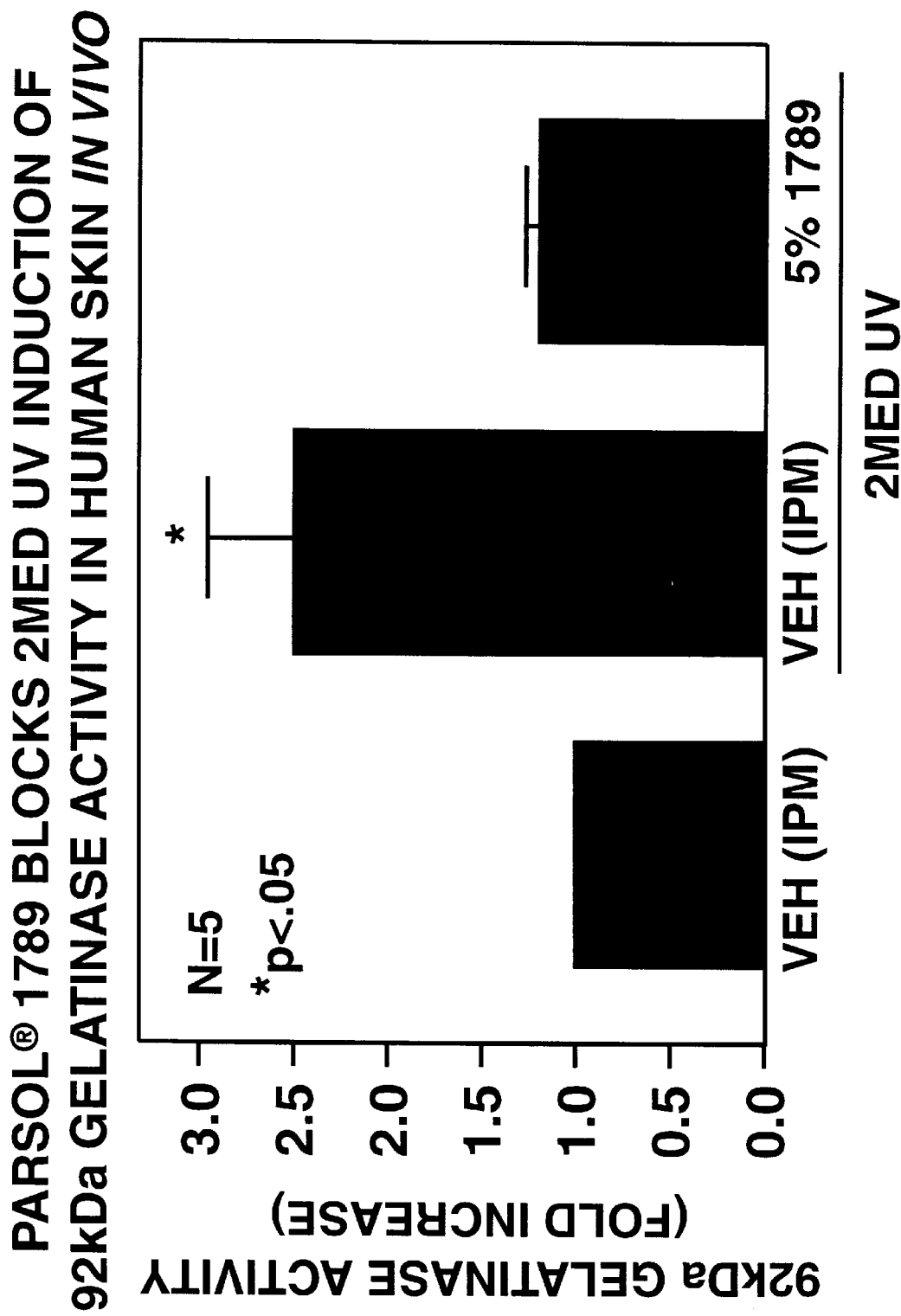
FIGS. 12 depicts the effectiveness of a particular UVA blocker for inhibiting UV-induced 92 kDa gelatinase in human skin.

Having shown above that UVA1 induces elevated levels of MMPs, UVA1 blockers are also useful at preventing this elevation (FIG. 12). These blockers may prevent initiation of the pathway(s) leading to increased MMP levels and/or activity, as they also prevent induction of c-JUN protein (data not shown).

Figure 13A:
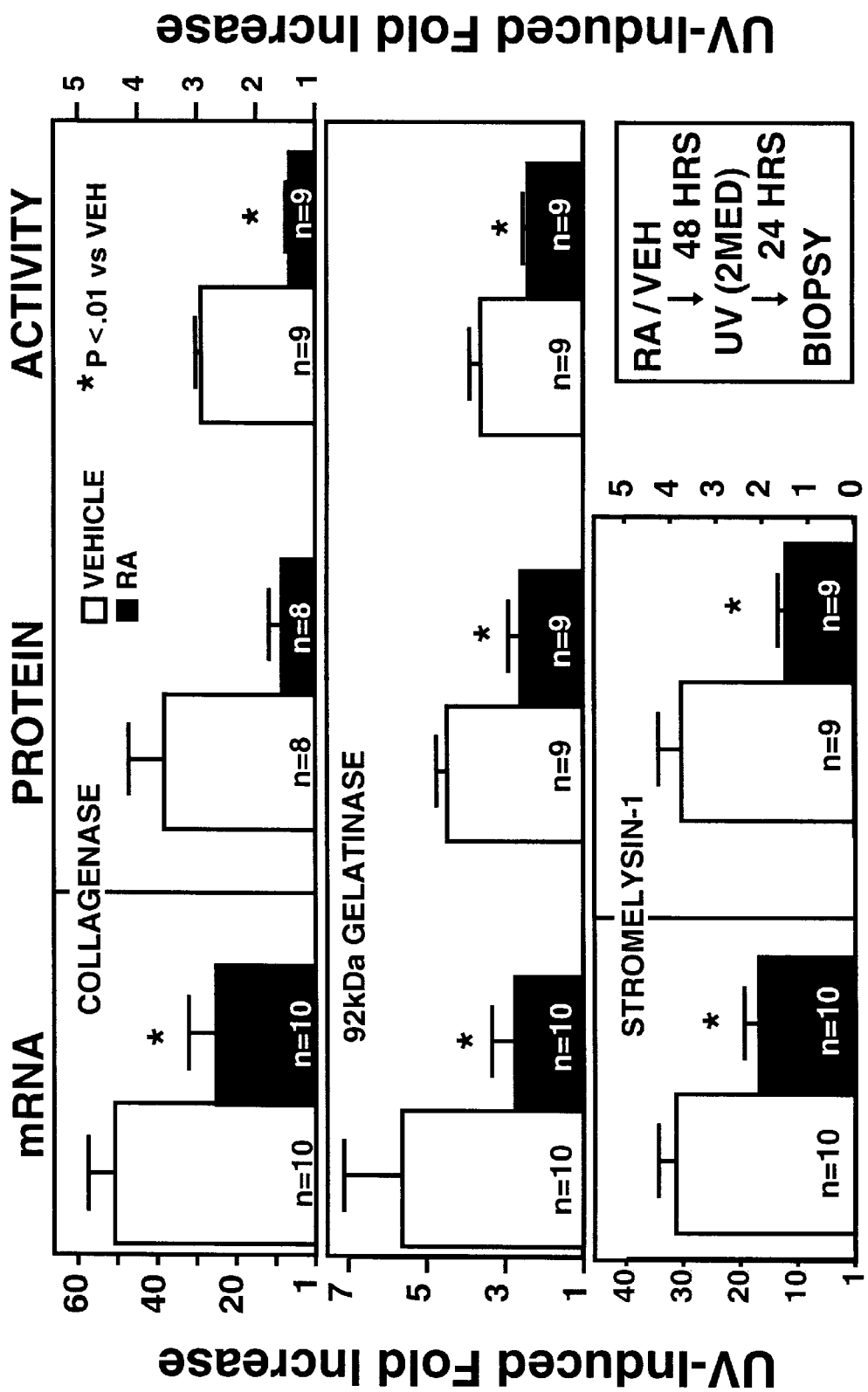
FIG. 13A depicts the effect of pretreatment with retinoids on the inhibition of UV-induced elevations in collagenase, the 92 kDa gelatinase, and stromelysin-1 in human skin upon exposure to 2 MEDs of radiation.
Figure 13B:
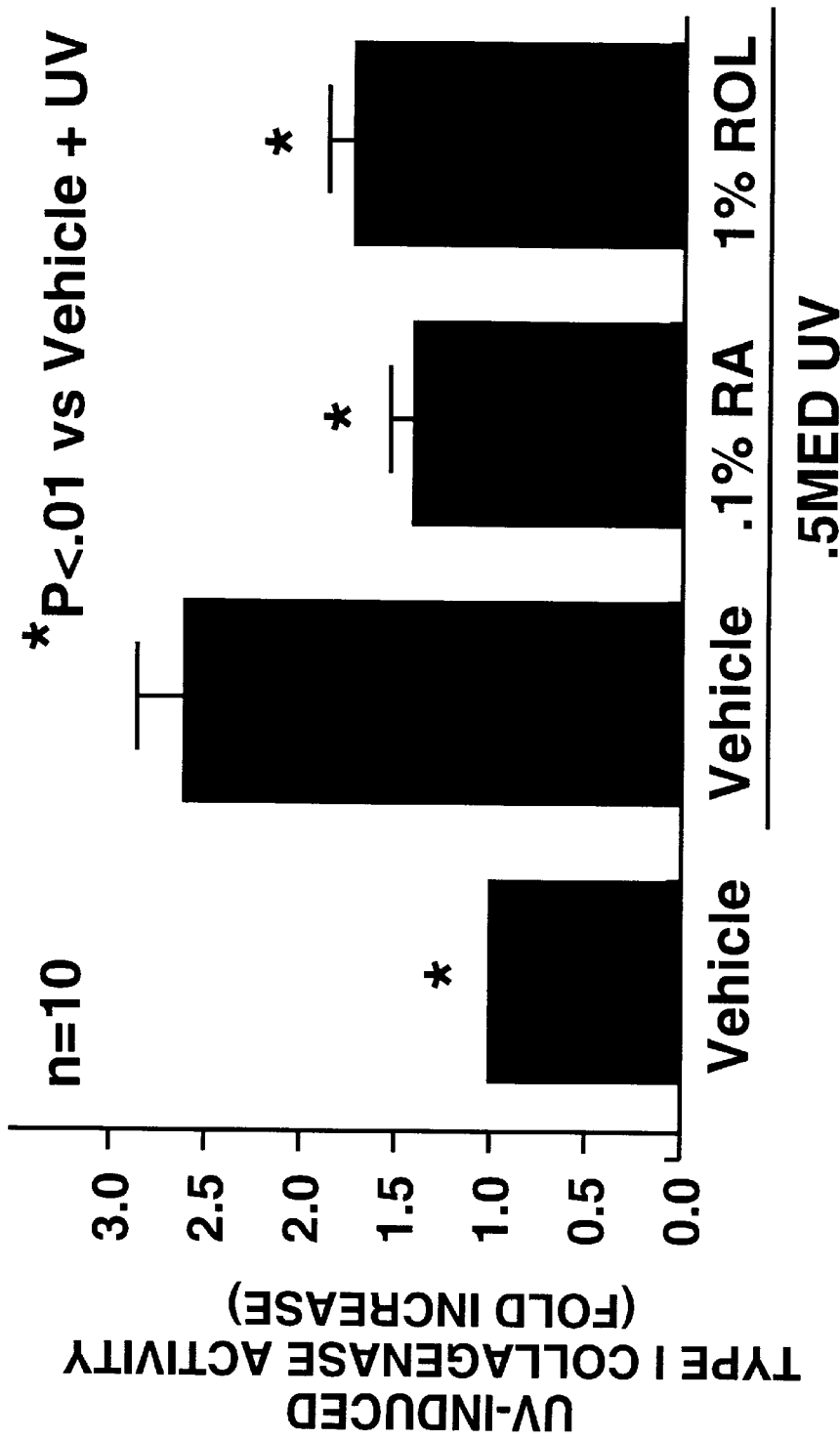
FIG. 13B depicts the effect of two different retinoids on subMED UV-induced increase in type I collagenase activity.

Retinoids are preferred inhibitors of UV-induced increases in the levels and/or activity of MMPs. Retinoic acid decreases 2 MED UVB-mediated induction of the levels and activity of the MMPs collagenase, 92 kDa gelatinase, and stromelysin-1, as well as their transcription (measured as mRNA) when applied 48 hours prior to exposure (FIG. 13A). Approximately ten times the concentration of retinol is about as effective as retinoic acid at preventing UV-induced elevation in type I collagenase activity, even at suberythemal radiation doses (FIG. 13B).

Figures 14A, 14B, 14C, 14D:
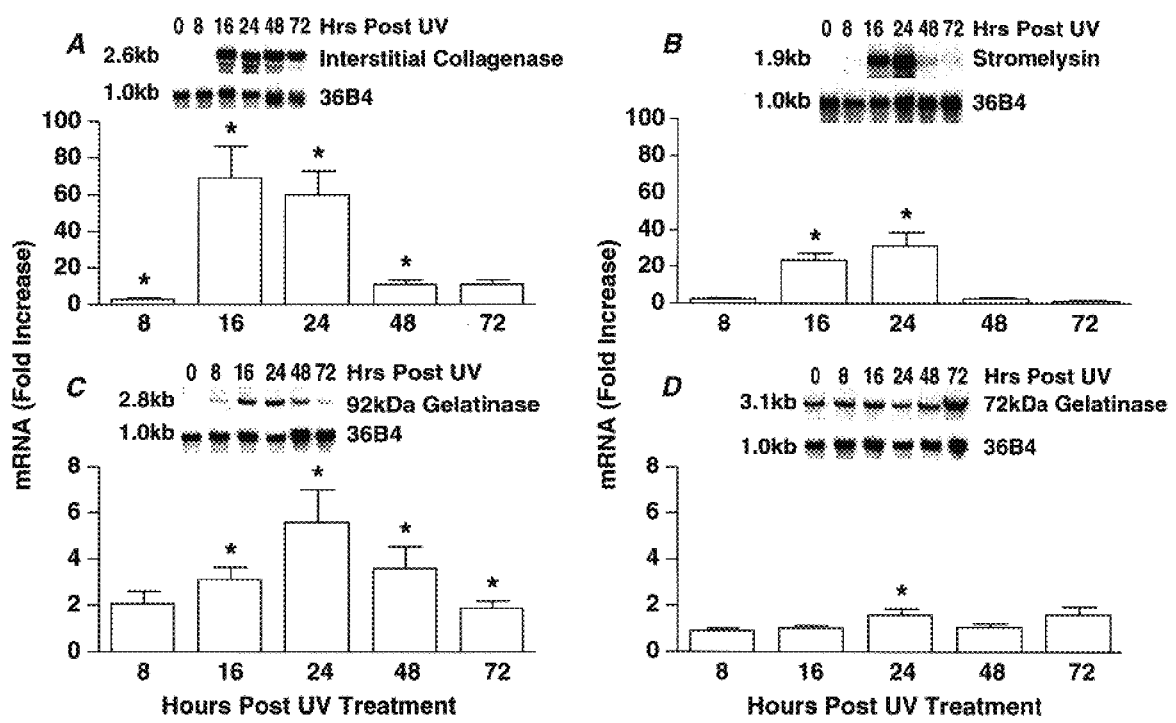
FIGS. 14A–14D depict the time course of the elevation of various MMPs (respectively collagenase, stromelysin, 92 kDa gelatinase, and 72 kDa gelatinase) in human skin after exposure to UV radiation.
Figure 15A:
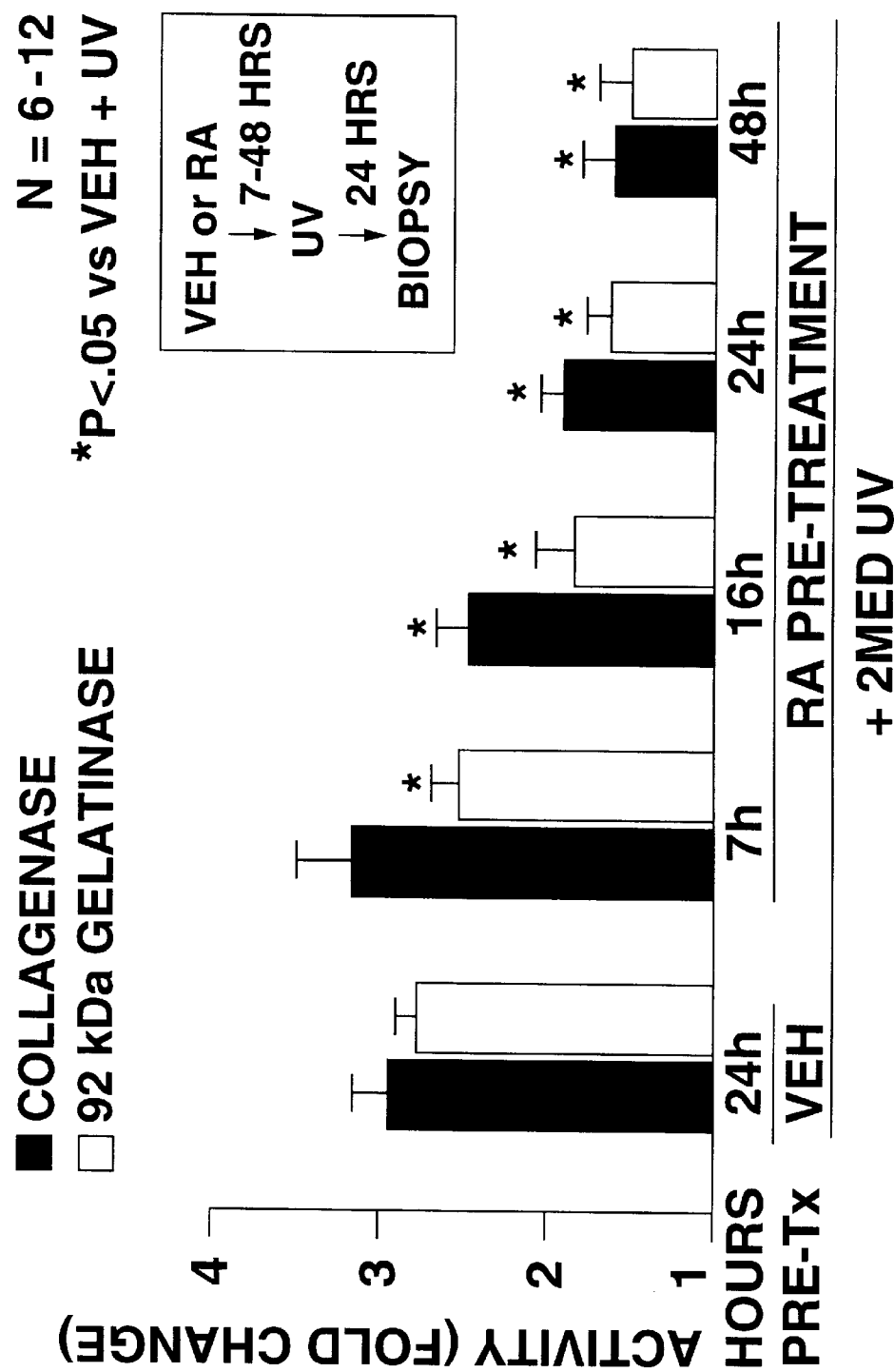
FIGS. 15A–15B depict the effect of the time of pretreatment on the effectiveness of retinoids for inhibiting UV-induced collagenase and the 92 kDa gelatinase, and of c-JUN protein.
Figure 15B:
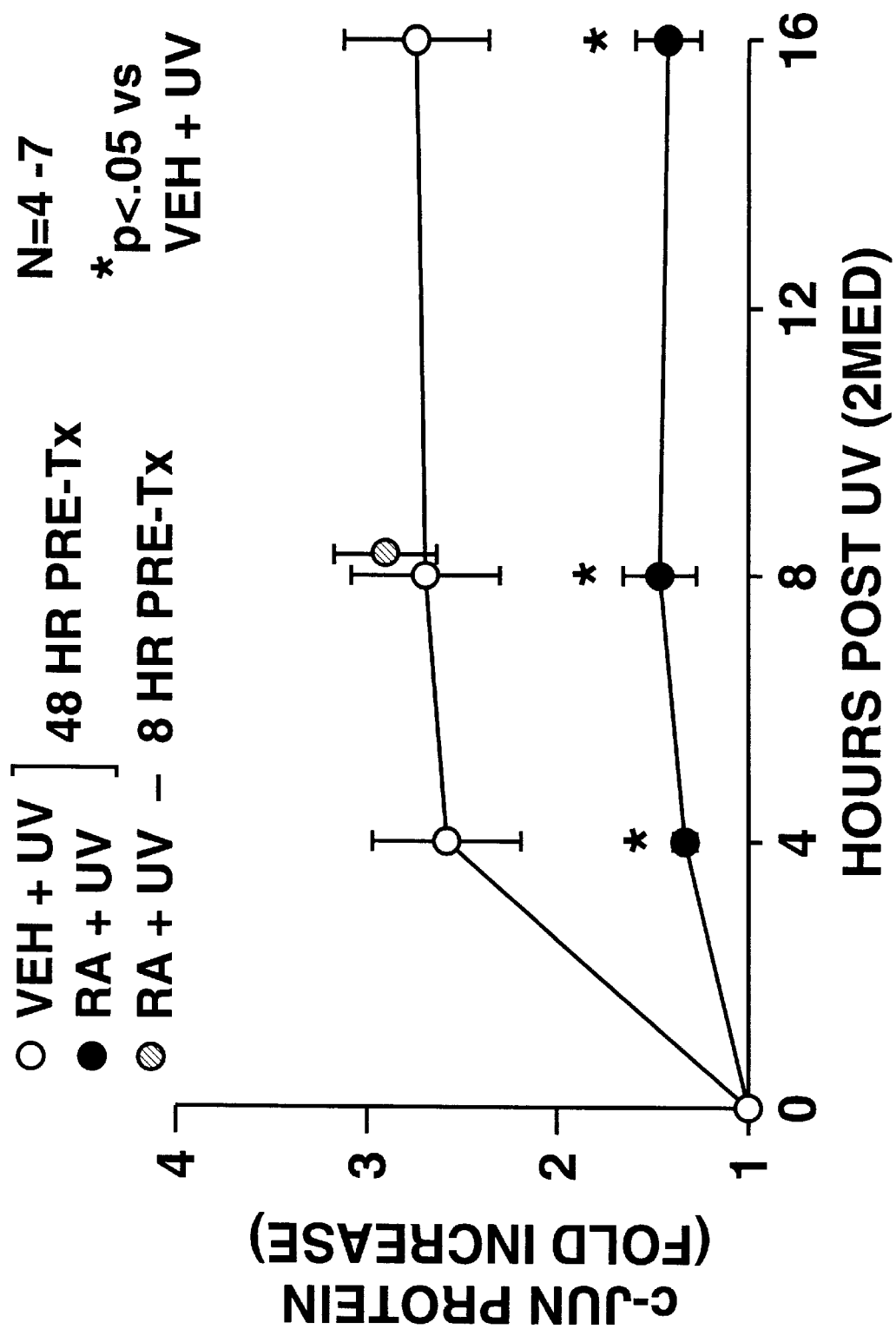

A single two MED UV exposure leads to increased MMP levels which are typically maximal about 24 hours after exposure (FIGS. 14A–14A; the same as FIGS. 2a–2d in our copending application 588,771). As with the various compounds found effective against erythema or UV-induced MMP activity, pretreatment is preferred when using retinoids, and the earlier the pretreatment before exposure, the better (FIG. 15A). Longer treatment times prevent, over time, the UV-mediated increase in c-JUN protein levels, which presumably lead to the increased MMP levels. In fact, the elevation in c-JUN protein levels appears to be severely limited when a retinoid is used about 48 hours prior to exposure (FIG. 15B). Although one might expect the time course of the levels of c-JUN protein to mirror the time course of those of the MMPs induced by UV exposure, those levels remain at a constant and only slightly elevated (compared with baseline, although they are signicantly below the levels induced in untreated, unprotected skin) when a retinoid is used as an MMP inhibitor. The decreased levels of c-JUN protein indicates that the retinoid decreases the production of MMPs over the entire time course studied rather than changing the kinetics of the UV-mediated skin reaction.

The present invention includes as a method for preventing photoaging of skin the daily topical application of a composition having both an MMP inhibitor and UVA/B blockers. As shown herein, and contrary to the present philosophy of this medical art, suberythemal UV exposure causes the generation of destructive proteinases. The vast majority of people daily spend some time in the daylight (be it walking the dog or walking to work), and because this is not the conventional "sun bathing", it would not have been expected that daily, suberythemal exposure to the sun causes photodamage as the result, in part, of UV-mediated increases in MMP activity. While a paleobiological explanation might be offered why human skin functions to create MMPs upon suberythemal UV exposure, our method of preventing, or at least inhibiting, at least this type of photoaging can be accomplished by the daily topical application of (i) a UVA/B blocker (i.e., broadly one or more compounds that block the direct effects of UVA/UVB radiation on the skin by absorbing, reflecting, or modulating the light to a non-harmful wavelength), (ii) a compound prophylactically effective to inhibit or reduce UV-induced MMP activity increase and/or a direct inhibitor of MMPs, and (iii) a compatible mixture of one or more of these ingredients. In view of these experiments, a preferred embodiment of our invention is an improved sunscreen composition which further comprises an MMP inhibitor, preferably a retinoid, and both a UVA blocker and a UVB blocker.

As used herein, "inhibitors" of MMPs inhibit one or more of the steps in the natural physiological pathways leading to MMP production and/or directly inhibit one or more of these proteinases. Thus, an MMP inhibitor can inhibit one or more of the various signalling compounds and/or of the transcription factors (e.g., cJUN and cFOS, which together lead to the production of MMPS) by which MMPs are produced naturally.

Retinoids are one class of MMP inhibitors. The inhibitors of MMPs can act directly on the MMPs and/or on the transcription factors AP-1 and NF-κB by which MMPs are produced naturally. E55 10 has been described (by Fujimori, T., et at., *Jpn. J. Pharmacol.* (1991) 55(1):81–91) as inhibiting NF-κB activation. Retinoids such as those disclosed in U.S. Pat. No. 4,877,805 and the dissociating retinoids that are specific for AP-1 antagonism (such as those described by Fanjul, et al. in *Nature* (1994) 372:104–110), glucocorticoids, and Vitamin $D_3$ target AP-1. Compounds for enhancing the therapeutic effect of Vitamin $D_3$ may also enhance the MMP-inhibitory effect of Vitamin $D_3$ and such are described in copending application Ser. No. 08/832,865 (J. Voorhees et al., "Method for Assessing $1,25(OH)_2D_3$ Activity in Skin and for Enhancing the Therapeutic Use of $1,25(OH)_2D_3$"), filed Apr. 4, 1997, the disclosure of which is incorporated herein by reference. Other retinoids, besides retinol, include natural and synthetic analogs of vitamin A (retinol), vitamin A aldehyde (retinal), vitamin A acid (retinoic acid (RA)), including all-trans, 9-cis, and 13-cis retinoic acid), etretinate, and others as described in EP-A2-0 379367, U.S. Pat. No. 4,887,805, and U.S. Pat. No. 4,888, 342 (the disclosures of which are all incorporated herein by reference). Various synthetic retinoids and compounds having retinoid activity are expected to be usefull in this invention, to the extent that they exhibit retinoid activity in vivo, and such are described in various patents assigned on their face to Allergan Inc., such as in the following U.S. Pat. Nos. 5,514,825; 5,698,700; 5,696,162; 5,688,957; 5,677, 451; 5,677,323; 5,677,320; 5,675,033; 5,675,024; 5,672, 710; 5,688,175; 5,663,367; 5,663,357; 5,663,347; 5,648, 514; 5,648,503; 5,618,943; 5,618,931; 5,618,836; 5,605, 915; 5,602,130. Still other compounds described as having retinoid activity are described in other U.S. Pat., Nos.: 5,648,563; 5,648,385; 5,618,839; 5,559,248; 5,616,712; 5,616,597; 5,602,135; 5,599,819; 5,556,996; 5,534,516; 5,516,904; 5,498,755; 5,470,999; 5,468,879; 5,455,265; 5,451,605; 5,343,173; 5,426,118; 5,414,007; 5,407,937; 5,399,586; 5,399,561; 5,391,753; and the like, the disclosures of all of the foregoing and following patents and literature references hereby incorporated herein by reference.

MMPs are also inhibited by BB2284 (described by Gearing, A. J. H. et al., *Nature* (1994) 370:555–557), GI129471 (described by McGeehan G. M., et al., *Nature* (1994) 370:558–561), and TIMPs (tissue inhibitors of metalloproteinases, which inhibit vertebrate collagenases and other metalloproteases, including gelatinase and stromelysin). Still other compounds useful for the present invention include hydroxamate and hydroxy-urea derivatives, such as Galardin, Batimastat, and Marimastat, and those disclosed in EP-A1-0 558635 and EP-A1-0 558648 (as useful for inhibiting MMPs in the treatment of, among other etiologies, skin ulcers, skin cancer, and epidermolysis bullosa). Retinoids have been reported by Goldsmith, L. A. (*Physiology, Biochemistry, and Molecular Biology of the Skin*, 2nd. Ed. (New York: Oxford Univ. Press, 1991), Chpt. 17) to cause an increase in steady state levels of TIMP mRNA that would suggest transcriptional control; although, based on our discoveries, we have found this is not true in human skin in vivo.

Other MMP inhibitors include genistein and quercetin (as described in U.S. Pat. No. 5637703, U.S. Pat. No. 5665367, and FR-A-2,671,724, the disclosures of which are incorporated herein by reference) and related compounds, as well as other antioxidants such as NAC (N-acetyl cystein), and others.

In addition to retinoids as a class of compounds useful for this invention, any drug which inhibits the cytochrome P-450 enzymes that metabolize retinoic acid can also be useful in practicing this invention. In the skin, retinoids are converted into retinoic acide (RA) as the active form. Natural retinoids that function in the skin are all trans or are metabolized to all trans. Retinoic acid (RA; all trans) is metabolized to inactivation by hydroxylation (via RA 4-hydroxylase) to 4-hydroxy-RA, which is then oxidized by a reaction mediated by the cytochrome P-450-dependent monooxygenase system. (S. Kang et al., "Liarozole Inhibits Human Epidermal Retinoic Acid 4-Hydroxylase Activity and Differentially Augments Human Skin Responses to Retinoic Acid and Retinol In Vivo," *J. Invest. Dermatol.*, 107:183–187 (Aug. 1996); E. A. Duell et al., "HumanSkin Levels of Retinoic Acid and Cytochrome P-450-derived 4-Hydroxyretinoic Acid after Topical Application of Retinoic Acid In Vivo Compared to Concentrations Required to Stimulate Retinoic Acid Receptor-mediated Transcription In Vitro," *J. Clin. Invest., Skin Retinoid Levels and Reporter Gene Activity*, 90:1269–1274 (Oct. 1992); E. A. Deull et al., "Retinoic Acid Isomers Applied to Human Skin in Vivo Each Induce a 4-Hydroxylase That Inactivates Only Trans Retinoic Acid," *J. Invest. Dermatol.*, 106:316–320 (Feb. 1996); the disclosures of which are incorporated herein by reference). Accordingly, compounds which interfere with the elimination metabolism of all trans RA, the active metabolite of topically applied retinoids such as 9-cis RA and 13-cis RA, will beneficially increase the amount of RA in the skin. Thus, preventing the degradation of natural (all trans) RA in the skin effectively increases its concentration, and so provides the benefits described herein. Examples of compounds dermatologically acceptable and having or likely to have inhibitory effects on the P-450-mediated degradation of RA include azoles, especially triazoles, including, for example, ketoconazole (U.S. Pat. Nos. 4,144, 346 and 4,223,036), fluconazole (U.S. Pat. No. 4,404,216), itraconazole (U.S. Pat. No. 4,267,179), liarozole, irtemazole, and the like; compounds related to these that may also be useful include, for example, diazines such as flucytosine. It would also be beneficial to use such cytochrome P-450 inhibitors in combination with a reduced amount of retinoid; the P-450 inhibitor decreases the metabolic elimination of the retinoid and so less retinoid is needed to achieve the same result. Still further, analytical methods are available for determining whether a given compound inhibits the degradation of RA by applying the compound and testing for changes in CRABP (cytoplasmic retinoic acid binding protein), which will have increased levels if the levels of RA are also increased by the topical application of the test compound.

Still other inhibitors of MMPs that can be applied topically and are useful in practicing the claimed invention include the tetracyclines and derivatives thereof, such as minocycline, roliteracycline, chlortetracycline, methacycline, oxytetracycline, doxycycline, demeclocycline, and the various salts thereof. Because of possible allergic or sensitization reactions, the topical adminstration of tetracyclines should be monitored carefully for such untoward reactions.

Various compounds termed "antioxidants" are also useful as MMP inhibitors. While not desirous of being constrained to any particular theory of operation, these compounds may quench or otherwise reduce free radicals and reactive oxygen species which may initiate or lead to MMP induction, such as via the MAP kinase cascade. These compounds include glutathione and its precursors, such as N-acetyl cysteine (NAC) or glutathione ethyl ester, more broadly $N-CH_3(CH_2)_nCO$ cysteine (wherein n is an integer from zero to eight, more preferably not more than 4), and related compounds and derivates thereof as described in U.S. Pat. No. 5,296,500 (the disclosure of which is incorporated herein by reference). These other MMP inhibitors include water-soluble compounds such as vitamin C and NAC, and FDO. Various other compounds that may act as MMP inhibitors include: lipid-soluble compounds such as β-carotene and its derivatives or other carotenoids; glutathione and derivatives thereof (or of NAC); α-lipoic acid (1,2-dithiolane-3-pentanoic acid); selenium compounds such as Ebselen (2-phenyl-1,2-benzisoselenazol-3(2 H)-one); isoflavones such as genistein (isoflavone), quercetin (flavon-3-ol), and pycnogenol (flavan-3-ol(s)); ergothioneine; saponin (e.g., from *Polypodium leucotomos*); ginkgo biloba extract (flavoneglycoside and terpenelactone) and feverfew (*Chrysanthemum parthenium*) extract (sesquiterpene lactone).

Various UV blockers are known in the paint and dye industry to prevent pigment or color degradation of cars, homes, and clothing. A particularly preferred $UVA_{1/2}$- blocker for use on human skin is PARSOL® 1789 (Schering-Plough), as well as those in the aforementioned U.S. Pat. No. 4,387,089 that describes the preparation of this UVA-blocker. We have found that true UVA blockers inhibit induction of cJUN mRNA and of collagenase and gelatinase.

The compositions of this invention can be provided in any cosmetically suitable form, preferably as a lotion or cream, but also in an ointment or oil base, as well as a sprayable liquid form (e.g., a "hair" spray that protects hair and scalp against UV damage, in a base that dries in a cosmetically acceptable way without the greasy appearance that a lotion or ointment would have if applied to the hair). In addition, the compositions contemplated by this invention can include one or more compatible cosmetically acceptable adjuvants commonly used, such as colorants, fragrances, emollients, humectants, and the like, as well as botanicals such as aloe, chamolile, and the like. When used topically, retinoids are used preferably at concentrations of between about 0.05% and about 5%, more preferably between 0.1% and 1%. Retinoids and the various antioxidants described above can also be taken systemically, preferably by oral administration. When dosed orally, retinoids are preferably administered in amounts from about 0.1 mg/kg (of body weight) to about 1 mg/kg or even more, all doses below that at which toxicity is likely; and antioxidants are preferably taken in "megadoses" (e.g., at least 1 g/d of vitamin C, at least 1000 I.U. of one or more tocopherols).

In summary, our invention is broadly viewed as refocussing the concept of preventing "photoaging" from preventing sunburn to preventing the increase in MMP activity following UV exposure. Our invention provides prophylaxis against photoaging through one or more modes: blocking UVA/B radiation at the level of the skin by use of a UVA/B blocking sunscreen; blocking the generation by UV radiation of reactive oxygen species in the skin that initiate the MAP kinase cascade and MMP induction by the topical application of an antioxidant; blocking the induction of transcription factors leading to increased MMP activity after UV exposure by the topical application of a retinoid or an MMP inhibitor (as broadly defmed herein); directly inhibiting MMP activity by the topical application of an inhibitor thereof; and/or by blocking the transmission of UVA radiation through a window structure to human skin by providing in the structure, or in a coating on the structure, a UVA blocker.

In view of our discoveries, it is clear that UV radiation at suberythemal doses causes skin damage. Thus, while prescription glasses and most sunglasses include UV-reflective or -absorbing materials or coatings, another aspect of our invention is to provide UV-coatings, especially against transmission of UVA, on all types of glass, including not only prescription and sunglasses but also for windows for homes and offices and automobiles. In addition, because jet airliners fly extremely high in the atmosphere, passengers situated near windows may be exposed not only to UVA and UVB radiation, but also possibly to more damaging UVC radiation. Given the present description of our invention, one or ordinary skill in the art related to window coatings could readily identify a UVA blocker and incorporate such into a film-formable or curable (e.g., paint-like) coating for joining or lamination to a window structure. Thus, in another embodiment, this invention includes transparent and translucent polymeric structures having UV-reflective and/or -absorbtive coatings (especially UVA-blockers) therein and/ or compounds therein. Such structures include window-like and window-covering devices, such as plastic awnings for baby carriages and plastic shades (typically colored or tinted) hung up in store windows when the sun is low. Again, one of ordinary skill in the art of fabricating these types of structures can now readily provide a UVA blocker, incorporate such into a film-forming polymeric material (e.g., plasticized polyvinyl acrylate), and provide a transparent or translucent window structure that blocks the transmission of UVA radiation. In connection with UVA-blocking windows, as noted above the relative amounts of UVA and UVB change as a function of the sun's elevation in the sky. At lower elevations of the sun (i.e., the morning or evening sun, as opposed to the "midday" sun, zenith angle of 0°), the relative amount of UVA:UVB is increased compared with other times of day (e.g., noon). At these lower elevations, the relative amount of UVA to UVB can more than double. Thus, contrary to present suppositions that the midday sun causes the most damage, which suppositions are likely because the greater amount of UVB light at a higher zenith more easily causes a bad sunburn, our discovery that a combination of suberythemal UVB plus UVA radiation causes photodamage shows the importance of protecting against photodamage at other times of day. Thus, a broad spectrum UVA/B window coating would be useful in protecting drivers going to and/or from work each day in the morning and/or evening hours.

In the following examples, four F36T12 ERE-VHO UV bulbs were used to irradiate human skin. At all times, a Kodocel TA401/407 filter was mounted 4 cm in front of the bulbs to remove UVC radiation (<290 nm). Radiation intensity was monitored using an IL443 phototherapy radiometer and an SED240/UVB/W photodetector (International Light, Newbury, Mass.). Spectroradiometry was performed using an Optronic Labroatories OL 754 system. Total irradiance (290–800 nm) at about 43 cm (17 in.) from the source of four bulbs was about 1.5 mJ/cm$^2$·s (1.49×10$^{-3}$ W/cm$^2$). The radiation output from this bulb was determined by spectroradiometry to provide about 47% UVB and about 27% UVA (composed of about 9% UVA$_1$ (340–400 nm) and about 18% UVA$_2$ (320–340 nm)), the remainder being visible and IR radiation. An exposure of about 160 seconds under this set of four bulbs is equivalent to an exposure of one MED. Accordingly, when compared with natural sunlight which has 0.5% UVB and 6.5% UVA, it can be seen that the set of four bulbs used in these experiments provides far less UVA radiation than would exposure to the sun of an equivalent amount of UVB.

In the following examples, a "standard vechicle" of 30% PEG (polyethylene glycol) in 70% ethanol (with 0.05% BHT as preservative) was used. UV-induced degradation of skin collagen was assessed by radioimmunoassay of soluble cross-linked telopeptides. mRNA and protein levels of MMPs and either endogenous inhibitors (TIMPs) were determined by Northern and Western analyses, respectively. Collagenase activity was measured by degradation of type I [$^3$H] collagenase. MMP activities were measured by zymography.

EXAMPLE 1

Suberythemal Induction of AP-1

Nine caucasian adults were exposed on their buttocks region (i.e., skin normally not exposed to sunlight) to the UV radiation from the aforedescribed set of bulbs for various times, after which tissue samples were taken and analyzed. As shown in FIGS. 2 and 3, and using the aforementioned time of 2 minutes and 40 seconds (160 s) as one MED, various portions of these volunteers' skin were exposed to 0, 0.01, 0.05, 0.1, 0.5, 1, and 2 MED of bulb radiation. The biopsied dermal tissue samples from exposed (and 0 MED, unexposed) skin were assayed for the presence of AP-1 and the fold increase of binding to DNA encoding AP-1. As described by Angel, P., et al., Cell (1987) 49:729–739 and Sato, H. and Seiki, M., Oncogene (1993) 8:395–405, the production of certain MMPs is mediated by the transcription factor AP-1.

The results of the biopsies shown in these figures are startling. At suberythemal doses down to about at least 0.01 MED, AP-1 is induced at levels clearly greater than present in unexposed skin. These unexpected results lead us to believe that photodamage to human skin can be induced by suberythemal MED radiation doses including UVB and UVA, and accordingly humans everywhere can be protected against photoaging by the daily application of a sunscreen that blocks at least UVA and optionally also UVB.

EXAMPLE 2

Retinoid Prophylaxis of Suberythemal Collagenase Induction

As described in our copending application Ser. No. 588, 771 (referred to above and incorporated herein by reference) it has been shown that retinoids inhibit the induction of various MMPS, including collagenases, after erythemal doses of radiation.

Using the buttocks skin of ten volunteers, following the same general procedure as described above, each of these volunteers was pretreated with the standard vehicle alone, with 0.1% retinoic acid (RA), or with 1% retinol (ROL). Tissue samples from these volunteers were biopsied following pretreatment and after no exposure and after exposure to 0.5 MED from the set of four bulbs.

The results of these biopsies are shown in FIG. 13B, which depicts the pretreatment and exposure regime to the fold increase of type I collagenase in vivo for the ten volunteers. As shown by the results in this figure, pretreatment of human skin with a retinoid can inhibit suberythemal UV-induced collagenase activity. Consistent with the results shown in FIG. 2, suberythemal UV exposure causes a significant increase in collagenase activity.

The results of Examples 1 and 2 were unexpected and intriguing to us, and prompted us to question the present philosophy of skin protection and solar-induced skin damage. Throughout time, and in different cultures, where the tanned, "outdoors" look is not considered aesthetically appealing, such as in Elizabethan England and in many Oriental cultures (e.g., Japan, Korea), various compounds and compositions have been tried to prevent sun damage to skin and/or to induce a "protective" tan. We decided to test various compounds and compositions, both old and new, for their true in vivo effect on UV-exposed skin.

EXAMPLE 3

Effect of UV Exposure after Topical Pretreatment I

Melatonin is a hormone apparently mediated by the light-dark cycle of day-night. It has been proposed recently that melatonin might act as an antioxidant.

We evaluated six volunteers to determine the effect, if any, of topical melatonin on UV-induced erythema using the same general procedure as described. The various UV dose exposures and the erythematic response of each of these volunteers after a five (5) minute exposure is depicted in FIG. 9. The previously unexposed skin of each of these volunteers was pretreated with the standard vehicle alone or with 5% melatonin. The results in FIG. 9 show that after exposure to two (2) MED, erythema was induced in vehicle-treated skin and was not induced in melatonin-treated skin. Even when erythema was induced in melatonin-treated skin, it was present to a significantly lesser degree than in vechicle-treated UV-irradiated skin. Nevertheless, it should be kept in mind, as shown above, that lack of erythema does not necessarily correlate with lack of photodamage.

In another set of experiments, volunteers had areas of unexposed skin pretreated with vehicle alone or with 5% melatonin or with 5% vitamin E about seven hours prior to UV exposure. The areas were then exposed to about 2 MED of UV radiation, after which chromameter reading were taken to determine the degree of erythema and biopsies were taken to determine the activity of type I collagenase and the 92 kDa gelatinase. The results shown in FIG. 9 show that both melatonin and vitamin E significantly reduced the erythema when compared with vehicle-treated UV-exposed skin. Accordingly, while melatonin and vitamin E may be considered antioxidants, we have found that they provide a good anti-sunburn sunscreen effect. Also, as shown by the results shown in FIG. 10, melatonin and vitamin E did not function to inhibit the increased MMP activity in UV-exposed human skin.

EXAMPLE 4

Effect of UV Exposure after Topical Pretreatment II

Another theory for causes of photodamage relates to the generation of reactive oxygen species (ROS) and other free radicals by UV radiation, because UV radiation is known to create free radicals. Accordingly, we investigated whether such "antioxidants" as vitamin C (ascorbic acid), N-acetyl cysteine (NAC), and 2-furildioxime (FDO), as well as aspirin (acetyl salicylic acid, ASA), had any effect on erythema or photodamage via MMP induction.

Volunteers were pretreated 16 hours prior to exposure, the exposure and biopsies being performed as described in the previous examples. In one experiment, the volunteers' skin was pretreated with vehicle alone or with 5% ASA or with 3.5% vit. C. and tested using a chromameter for erythema and by zymography for collagenase activity. After a one (1) MED exposure, FIG. 9 shows that pretreatment with aspirin or vitamin C reduced the UV-induced erythema upon a one (1) MED exposure from that of untreated (vehicle-only-treated) skin, with aspirin providing about a 30% reduction in erythema versus that achieved by vitamin C, about 30% less than untreated skin. However, when the biopsies were evaluated for collagenase activity, the results of which are shown in FIG. 10, the aspirin-treated skin evidenced a greater collagenase activity than untreated skin, and vitamin C provided about a 25% reduction in collagenase activity with respect to untreated skin. Again, these surprising results show that erythema is not correlatable to MMP-mediated UV-induced photodamage to human skin. In fact, looking only at erythema, one may be tempted to use aspirin, but these results show that aspirin has no protective effect on photodegradation of skin as mediated by type I collagenase.

This same general experimental protocol was repeated at an exposure of two (2) MED using the vehicle alone, or with 20% NAC, or with 5% FDO, which compounds were also applied to the volunteers much prior to exposure. FIG. 9 depicts the results of the erythema analysis for these compounds, and shows that FDO completely inhibited erythema, while NAC had no effect (i.e., the same as the vehicle-treated skin). Unexpectedly again, however, analysis of type I collagenase activity at these same exposure levels, as shown in FIG. 10, evidences that NAC provided significant protection against collagenase activity, while FDO provided some protection against MMP induction.

EXAMPLE 5

Pretreatment Time Dependency

In addition to the general unpredictability of determining whether a given compound will inhibit erythema and/or MMP-mediated degradation of the skin after exposure to UV radiation, we have also discovered that there can be a time-dependent effect of the protection.

Volunteers' skin was exposed to one (1) MED using the four bulb set and was pretreated with vehicle alone, or with 20% NAC, either four hours or seven hours prior to exposure. Following exposure, chromameter and zymography analyses were performed as previously described.

NAC provided no anti-redness effect on UV-exposed skin, regardless of the duration of pretreatment. FIGS. 11A and 11B show, in comparison with the results shown in FIG. 9, the unexpected effect on type I collagenase after pretreatment with NAC and exposure to 1 MED. A seven hour pretreatment with NAC provided an inhibitory effect on the UV-induced increase in the 92 kDa gelatinase (FIG. 11A) and collagenase (FIG. 11B) activities when compared with untreated skin (which showed over 150% increase in collagenase activity), whereas a four hour pretreatment was ineffective.

EXAMPLE 6

Effect of Commercial Sunscreens

We also evaluated commercially available sunscreens for their effect on UV-induced erythema and collagenase activity. Volunteers' skin was pretreated with the standard vehicle and with three sunscreens (on different areas of skin): an SPF (sun protection factor) 15 composition including ethylhexyl p-methoxycinnamate and oxybenzone; an SPF 30 composition stated on the packaging to provide UVA and UVB protection and comprising octocrylene (10%), octyl methoxycinnamate (7.5%), and oxybenzone (6%); and an SPF 50 composition stated on the packaged to provide UVA and UVB protection and comprising higher amounts of the same components as the SPF 30 composition.

After pretreatment with the vehicle and the sunscreen on different areas of skin, and then exposure to two (2) MED, the volunteers' skin was evaluated for erythema. As the results in FIG. 7 show, all of the commercially available sunscreens provided excellent protection against UV-induced erythema; there was essentially no redness in comparison with unexposed skin.

EXAMPLE 7

Physiological Effect of Regular Suberythemal UV Exposure

We examined the effect of repeated suberythemal UV dosing on the induction of MMPs, specifically type I collagenase and the 92 kDa gelatinase, in vivo. Volunteers were irradiated at 0.5 MED on four separate sites, with each cite receiving one, two, three, or four UV exposures, the exposures being separated by 48 hour intervals. Skin was biopsied from each volunteer twenty four hours after the last exposure, including skin from a non-irradiated area (used as control), and analyzed for MMP activity. As shown in FIG. 3, collagenase and gelatinase activities were elevated 2.2-fold and 4.4-fold, respectively, after a single UV exposure, and remained elevated at essentially these same levels upon repeated exposure every other day for four days.

While we have shown that application of a retinoid (especially trans-retinoic acid, tRA) can, post-UV exposure, decrease MMP activity in the skin, we also investigated the effect of pretreatment with tRA before exposure. Treatment of skin with tRA did not alter the low basal levels of collagenase, the 92 kDa gelatinase, or stromelysin, and subsequent irradiation with UV lead to substantial reduction in the level of these three MMPs in retinoid pretreated skin in comparison with unpretreated skin. Volunteers were exposed to various UV doses ranging from 0.01 to 2 MED and biopsies taken from these and an unexposed area. As shown in FIGS. 2, 3, and 14A–14D, stromelysin-1 was induced within eight hours after exposure at a quite low, suberythemal, exposure level; induction was clearly evident at 0.1 MED. After these exposures, 0.1% tRA was applied daily for three days to the exposed areas and biopsies were taken again. As shown in FIG. 13B, tRA did cause a significant reduction in stromelysin-1 protein.

EXAMPLE 8

Effect of UV Wavelength on MMP Induction

We investigated the effect of pretreatment of skin with a known UVA blocker on both erythema and MMP activity after exposure to 2 MEDs of UV radiation. In particular, we used PARSOL® 1789 (also known as PARSOL A) brand of 4-t-butyl-4'-methoxydibenzoylmethane, which is described in U.S. Pat. No. 4,387,089 (the disclosure of which is incorporated herein by reference). (PARSOL MCX and PARSOL MOX are trademarks for 2-ethylhexyl p-methoxycinnamate, a UVB blocker commonly used in commercial sunscreen, and disclosed in U.S. Pat. No. 4,713,473, the disclosure of which is incorporated herein by reference). The absorbance characteristics of PARSOL® 1789 over the $UVA_1$, $UVA_2$, and UVB wavelengths is shown as the dotted line in FIG. 8A. As shown therein, this compound is especially useful at blocking $UVA_2$ radiation and somewhat effective at blocking $UVA_1$, radiation. The shaded line shows the wavelengths of natural erythemogenic UV radiation; as seen, erythema is caused primarily by UVB radiation.

In a set of experiments, volunteers had areas of unexposed skin pretreated with a vehicle alone or with 5% of the PARSOL® 1789 UVA blocker. These pretreated areas were exposed to about 2 MED of UV radiation, and later tested for erythema, and biopsied to test for activity of the 92 kDa gelatinase and the presence of cJUN protein.

FIG. 8B shows the results of post-exposure testing for sunburn, in which PARSOL® 1789 pretreated skin was not protected from sunburn induced by UV exposure. Based on the significant blocking of UVA radiation by PARSOL® 1789, these results confirm that UVB radiation is the primary culprit in sunburn.

FIG. 12 shows the results of in vivo activity assays of the gelatinase in the volunteers' skin, which activity was significantly reduced in UV-exposed PARSOL® 1789-pretreated skin when compared with UV-exposed vehicle-treated skin. In fact, the gelatinase activity in the UVA blocker-treated skin was not significantly different from vehicle-treated unexposed skin. These results show that UVA is a clear cause of UV-mediated MMP induction in UV-exposed skin. Accordingly, only certain wavelengths of UV radiation are prone to causing photoaging and photodegradation of skin. Thus, our invention includes the prevention of photoaging by the use of a UVA-blocking sunscreen.

EXAMPLE 9

As shown above, there can be a delay between the application of the active ingredient to the skin and its ability to inhibit MMPs or its precursors in vivo. Shown in FIG. 15A are the results of time course study of the topical application of RA and its effects on the inhibition of collagenase, gelatinase, and cJUN protein upon exposure to UV radiation.

Volunteers were pretreated with vehicle alone, or with vehicle plus 0.1% RA at 7, 16, 24, and 48 hours prior to exposure of the skin to 2 MED of UV radiation, and 24 hours after exposure biopsies were taken from the exposed portion of the volunteers' skin. As shown in FIG. 18A, pretreatment with the vehicle alone 24 hours prior to exposure provides a baseline activity for the collagenase and gelatinase. Pretreatment with RA seven hours prior to exposure did not yield activities for the collagenase or gelatinase significantly different than the vehicle alone. At 16 hours pretreatment, the collagenase activity is not much different from that with pretreatment with the vehicle alone, but the gelatinase activity is clearly decreased. At 24 hours pretreatment, both the collagenase and gelatinase activities are significantly lower than their activities when only the vehicle was used. At 48 hours pretreatment, the collagenase and gelatinase activities are reduced even further.

Investigation was also made to determine whether the amount of cJUN protein in skin exposed to UV radiation changed depending on whether (1) the skin was pretreated 48 hours before exposure with (a) the vehicle alone or (b) with RA in the vehicle, and (2) at 8 hours before exposure with RA dispersed in the vehicle. As seen from FIG. 15B, pretreatment with RA eight hours before exposure did not cause any change in the amount of cJUN in the skin compared with pretreatment (48 hrs pre-exposure) with the vehicle alone. On the other hand, pretreatment with RA 48 hours before exposure yielded a significant reduction in the amount of CJUN protein in the skin. In view of the pathway shown in FIG. 1, an increase in the amount of cJUN in the skin would be expected to result in increased AP-1 concentrations and, inevitably, an increase in MMPs with concomitant tissue degradation.

In view of these results, when a retinoid is used as the active ingredient to inhibit photoaging, it is preferred to apply the retinoid to skin more than 8 hours, more preferably at least 16 hours, even more preferably at least 24 hours, and even up to 48 hours prior to exposure to UV radiation. As shown in our prior application 588,771, the activities of collagenase and gelatinase can take a significant amount of time to increase from their base levels, up to 48 hours, after exposure to UV radiation. The results shown in this example now indicate that it can also take a not insignificant amount of time for topically applied retinoids to down regulate the MMP pathway. Thus, a preferred method for inhibiting photoaging is using the present compositions the day prior to the day during which protection is desired, and most preferably the present compositions are used daily, so that photoaging is always inhibited (especially when, as we have shown, that incidental, suberythemal UV doses up-regulate MMP activity).

METHODS USED IN THE EXAMPLES

The references noted in this section are incorporated herein by reference.

Preparation of skin supernatants for biochemical analysis. Skin samples were ground by mortar and pestle under liquid nitrogen, and homogenized in a Dounce tissue grinder in buffer containing 10 mM Hepes, 1 mM EDTA, 5 mM EGTA, 10 mM $MgCl_2$, 50 mM glycerophosphate, 5 mM $NaVO_4$, 2 mM DTT, 0.5 mM PMSF, 10 μg/ml aprotinin, 10 μg/ml leupeptin, and 10 μg/ml pepstatin, and 0.5% NP-40. Homogenates were centrifuged at 14,000 g for 15 min., and supernatants were collected and used for biochemical determinations as described herein.

Matrix metalloproteinase assays. Tissue pieces were frozen in liquid nitrogen immediately after biopsy, homogenized in 20 mM Tris HCl (pH 7.6) plus 5 mM $CaCl_2$, and centrifuged at 3000× g for 10 minutes to remove particulates. Ability to release soluble radioactive fragments from 3 H-labeled fibrillar Type I collagen (described by Fisher, G. J., et al., Nature, 379, 335–339 (1996) and Hu, C-L, et al., Analytic. Biochem, 88, 638–643 (1978)) was used as a measure of collagenolytic activity. Tissue extracts were incubated for 3 hours with 1 mM aminophenyl mercuric acetate (APMA) to convert the inactive form of the matrix metalloproteinase into an active form. Subsequently, 0.2 $\mu$Ci of collagen substrate (NEN-DuPont, Boston, Mass.) was incubated for 24 hours with 50 $\mu$l of tissue extract. At the end of the 24-hour incubation period, the samples were centrifuged at 12,000×g for 10 minutes to pellet the intact protein. Radioactivity remaining in the supernatant fluid was then measured and from this, the percentage of substrate hydrolzyed was determined.

Gelatin zymography (Varani et al., op. cit.) was used to assess MMP-2 (72-kD gelatinase; gelatinase A) and MMP9 (92-kD gelatinase; gelatinase B) activity. Tissue extracts were electrophoresed in an 8.5% SDS-polyacrylamide gel containing 1 mg/ml of gelatin. After electrophoresis, the SDS was removed by three sequential washes in 1% Triton X-100. The first two washes were for 20 minutes each and the last was overnight. Quantitation of hydrolysis zone width was done by laser densitometry.

c-Jun kinase activity assay. c-Jun activity in skin supernatants was determined by solid phase kinase assays (as described, e.g., by M. Hibi et al., "Identification of an oncoprotein and UV-responsive protein kinase that binds and potentiates the c-Jun activation domain," Genes Dev., 7:2135–2148 (1993)).

Northern analysis of RNA. Total RNA (e.g., for c-Jun) was isolated from skin samples by guanidinium hydrochloride lysis and ultracentrifugation (as described by G. J. Fisher et al., "Cellular, immunologic and biochemical characterization of topical retinoic acid-treated human skin," J. Investig. Dermatol., 96:699–707 (1991)). Northern analysis of total RNA (40 $\mu$g/lane) with randomly primed $^{32}P$ labelled cDNA probes for the particular mRNA to be determined were performed as described by G. J. Fisher et al. (in "All trans retinoic acid induces cellular retinol-binding protein in human skin in vivo," J. Investig. Dermatol., 105:80–86 (1995)).

Western analysis of proteins. Jun proteins were detected in nuclear extracts from human skin by Western analysis as described by G. J. Fisher et al. (in "Immunological identification and functional quantitation of retinoic acid and retinoid X receptor proteins in human skin," J. Biol. Chem., 269:20629–20635 (1994)). Immunoreactive proteins were visualized by enhanced chemiluminescence detection and quantified by laser densitometry, or by enhanced chemifluorescence detection and quantified by a Storm imager (Molecular Dynamics, Palo Alto, Calif.).

Chromameter: erythema (skin reddening) was determined 24 h post-exposure using a commercially available Minolta chromameter (chromameter CR200, model 94401085).

The foregoing description is meant to be illustrative and not limiting. Various changes, modifications, and additions may become apparent to the skilled artisan upon a perusal of this specification, and such are meant to be within the scope and spirit of the invention as defined by the claims.

What is claimed is:

1. A composition for inhibiting photoaging of human skin, comprising a combination of a UVA1 blocker preventing penetration of UV light having a wavelength between about 360 nm and 400 nm, a UVB blocker preventing penetration of UV light having a wavelength of between about 300 and 320 nm, an amount of an MMP inhibitor effective to inhibit the UV-induction of increased MMP activity, and a topically acceptable carrier.

2. The composition of claim 1, wherein the MMP inhibitor is a retinoid.

3. The composition of claim 1, further comprising a compound selected from the group consisting of N-acetyl cysteine, FDO, vitamin C, and mixtures thereof.

4. The composition of claim 1, wherein the UVA1 blocker is 4-t-butyl-4'-methoxydibenzoylmethane or a derivative thereof.

5. The composition of claim 1, wherein the UVB blocker is an oxybenzone or a methoxycinnamate.

6. The composition of claim 1, formulated as a lotion, cream, ointment, water-based liquid, oil-based liquid, or sprayable liquid.

7. The composition of claim 2, wherein the retinoid is retinoic acid or retinol.

8. The composition of claims 1, wherein said composition further comprises at least one additional compound selected from the group consisting of tetracycline and derivatives thereof, dermatologically acceptable triazoles and derivatives thereof, a compound that inhibits the cytochrome P-450 mediated-metabolism of retinoic acid, and compatible mixtures thereof.

9. The composition of claim 1, provided as a day and night combination of compositions for inhibiting photoaging of human skin induced by UV radiation, comprising:

a first composition for use during the day and comprising the composition defined by claim 1; and further comprising a second composition for use during the evening, said second composition comprising an MMP inhibitor in a dermatologically acceptable carrier;

wherein said first and second compositions are provided together and packaged separately from each other, and further comprising instructions for the use of said first and second compositions.

10. The day and night combination of claim 9, wherein the MMP inhibitor in each of said first and second compositions is selected independently from the group consisting of a retinoid, N-acetyl cysteine, 2-furildioxime, vitamin C, and mixtures thereof, in a dermatologically acceptable carrier.

11. The composition of claim 10, where the retinoid in the first composition, the second composition, or both, is selected independently from the group consisting of retinoic acid, retinol and mixtures thereof.

* * * * *